United States Patent [19]

Dean et al.

[11] Patent Number: 5,585,377
[45] Date of Patent: Dec. 17, 1996

[54] SULFONAMIDES USEFUL AS CARBONIC ANHYDRASE INHIBITORS

[75] Inventors: Thomas R. Dean, Weatherford; Jesse A. May; Hwang-Hsing Chen, both of Fort Worth, Tex.

[73] Assignee: Alcon Laboratories, Inc., Fort Worth, Tex.

[21] Appl. No.: 362,716

[22] Filed: Dec. 23, 1994

Related U.S. Application Data

[63] Continuation-in-part of Ser. No. 19,011, Feb. 18, 1993, Pat. No. 5,378,703, which is a continuation-in-part of Ser. No. 775,313, Oct. 9, 1991, Pat. No. 5,240,923, which is a continuation-in-part of Ser. No. 618,765, Nov. 27, 1990, Pat. No. 5,153,192, which is a continuation-in-part of Ser. No. 506,730, Apr. 9, 1990, abandoned.

[51] Int. Cl.$^6$ .................... C07D 513/04; A61K 31/54
[52] U.S. Cl. .......................... 514/226.5; 544/48
[58] Field of Search ............... 514/226.5; 544/48

[56] References Cited

U.S. PATENT DOCUMENTS

| | | | |
|---|---|---|---|
| 4,619,939 | 10/1986 | Maren | 514/363 |
| 4,731,368 | 3/1988 | Hoffman, Jr. et al. | 514/301 |
| 4,746,745 | 5/1988 | Maren | 548/139 |
| 4,797,413 | 1/1989 | Baldwin et al. | 514/432 |
| 4,847,289 | 7/1989 | Baldwin et al. | 514/445 |
| 5,153,192 | 10/1992 | Dean et al. | 544/48 |
| 5,240,923 | 8/1993 | Dean et al. | 544/48 |
| 5,378,703 | 1/1995 | Dean et al. | 544/48 |

FOREIGN PATENT DOCUMENTS

| | | |
|---|---|---|
| 1096916 | 1/1961 | Germany. |
| 1516024 | 6/1978 | United Kingdom. |

OTHER PUBLICATIONS

"The Reactions of Some Thiophene Sulfonyl Derivatives", Cremyln et al., *Phosphorus and Sulfur*, vol. 10, pp. 111–119, 1981.

"Studien in der Thiophenreihe. XXIV.$^2$ Uber Nitrothiophene and Thiophensulfochloride", Steinkopf et al., *Justus Liebigs Analen Der Chemie*, vol. 501, pp. 174–188, 1933.

"Heterocyclic Disulponamides and Their Diuretic Properties", deStevens et al., *Journal of Medicinal and Pharmaceutical Chemistry*, vol. 1(6), pp. 565–576, 1959.

Gronowitz et al., *Thiophene and its Derivatives*, vol. 44, Pt. 3, pp. 135–307. (1986).

*Primary Examiner*—John M. Ford
*Attorney, Agent, or Firm*—Sally Yeager

[57] ABSTRACT

Sulfonamides and pharmaceutical compositions containing the compounds useful in controlling intraocular pressure are disclosed. Methods for controlling intraocular pressure through administration of the compositions are also disclosed.

6 Claims, No Drawings

SULFONAMIDES USEFUL AS CARBONIC ANHYDRASE INHIBITORS

This application is a continuation-in-part of U.S. Ser. No. 08/019,011, filed Feb. 18, 1993, now U.S. Pat. No. 5,378,703, which is a continuation-in-part of U.S. patent application Ser. No. 07/775,313, filed Oct. 9, 1991 (now U.S. Pat. No. 5,240,923), which is a continuation-in-part of U.S. patent application Ser. No. 07/618,765, filed Nov. 27, 1990, now U.S. Pat. No. 5,153,192, which is a continuation-in-part of U.S. patent application Ser. No. 07/506,730, filed Apr. 9, 1990, now abandoned.

FIELD OF THE INVENTION

The present invention relates to new sulfonamides useful in lowering and controlling intraocular pressure.

BACKGROUND OF THE INVENTION

Glaucoma is a disease of the eye which is characterized by a progressive loss of visual field due to irreversible damage to the optic nerve to the point where if untreated can result in total blindness. This loss of visual field, in one form of primary open angle glaucoma, or POAG, is associated with a sustained increase in the intraocular pressure (IOP) of the diseased eye. Moreover, elevated intraocular pressure without visual field loss is thought to be indicative of the early stages of this form of POAG.

There are a number of therapies that target reducing the elevated IOP associated with this form of POAG. The most common feature the topical administration of a beta adrenergic antagonist or a muscarinic agonist. These treatments while effective in lowering IOP can also produce significant undesirable side effects.

Another less common treatment for this form of POAG is the systemic administration of carbonic anhydrase inhibitors. However, these drugs also can bring about unwanted side effects, such as nausea, dyspepsia, fatigue, and metabolic acidosis.

U.S. Pat. Nos. 4,797,413, 4,847,289 and 4,731,368 disclose topically dosed thiophene sulfonamides which lower IOP by inhibiting carbonic anhydrase.

Thiophene bis-sulfonamides, which are carbonic anhydrase inhibitors useful for treating conditions attributable to a restriction of blood flow to the brain, including atherosclerosis, occlusion of blood vessels in the brain, stroke and other cerebra vascular diseases, are disclosed in the British Patent No. 1,516,024. Similar compounds are also disclosed in *Justus Liebigs Annalen der Chemie*, 1933, 501, 174–188 and in *Phosphorus Sulfur*, 1981, 10(1), 111–119.

Other thiophene bis-sulfonamides, which are carbonic anhydrase inhibitors useful as diuretics, are disclosed in the German Patent No. 1,096,916 and *Journal of Medicinal and Pharmaceutical Chemistry*, 1959, 1(6), 565–576.

The compounds of the present invention are new sulfonamides which are carbonic anhydrase inhibitors (CAIs) useful for lowering IOP without producing significant systemic side effects when delivered topically to the eye.

SUMMARY OF THE INVENTION

The present invention is directed to new sulfonamides which can be used to lower and control IOP. The compounds are formulated in pharmaceutical compositions for delivery.

The preferred compounds of this invention are effective in lowering and controlling IOP when administered at unexpectedly low doses. Moreover, topical administration of these low dosages has the added advantage of providing for a superior comfort profile. In general, these compositions are substantially more comfortable than that observed with previous topical CAIs. It is expected that these improvements will lead to more effective therapies for the treatment of elevated IOP and glaucoma.

The invention is also directed to methods for lowering and controlling IOP by the administration of the compositions comprising the sulfonamides of the present invention. The compositions can be administered systemically and/or topically to the eye.

DETAILED DESCRIPTION OF THE INVENTION

The sulfonamides of the present invention have the following structure.

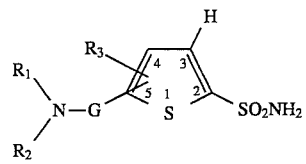

or a pharmaceutically acceptable salt thereof wherein:

$R_1$ is H; $C_{1-4}$ alkyl; $C_{2-4}$ alkyl substituted optionally with OH, halogen, $C_{1-4}$ alkoxy or $C(=O)R_7$.

$R_2$ is H; $C_{1-8}$ alkyl; $C_{2-8}$ alkyl substituted with OH, $NR_5R_6$, halogen, $C_{1-4}$ alkoxy, $C_{2-4}$alkoxy$C_{1-4}$alkoxy, $OC(=O)R_7$, or $C(=O)R_7$; $CH_2COR_7$; $C_{3-7}$ alkenyl unsubstituted or substituted optionally with OH, $NR_5R_6$, or $C_{1-4}$ alkoxy; $C_{3-7}$ alkynyl unsubstituted or substituted optionally with OH, $NR_5R_6$, or $C_{1-4}$ alkoxy; $C_{1-3}$ alkyl substituted with phenyl or $R_{10}$ either of which can be unsubstituted or substituted optionally with $C_1$–$C_3$alkyl, $C_1$–$C_3$halo alkyl, OH, $(CH_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0–2 and n is 0–2; $C_{2-4}$ alkoxy substituted optionally with $NR_5R_6$, halogen, $C_{1-4}$ alkoxy, or $C(=O)R_7$; phenyl or $R_{10}$ either of which can be unsubstituted or substituted optionally with $C_1$–$C_3$alkyl, $C_1$–$C_3$halo alkyl, OH, $(CH_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0–2 and n is 0–2; provided that $R_1$ and $R_2$ cannot both be H; or $R_1$ and $R_2$ can be joined to form a saturated ring of 5 or 6 atoms selected from O, S, C or N, such as, pyrrolidine, oxazolidine, thiomorpholine, thiomorpholine 1,1 dioxide, morpholine, piperazine, thiazolidine 1,1 dioxide, or tetrahydrooxazine, which can be unsubstituted or substituted optionally on carbon with OH, $NR_5R_6$, halogen, $C_{1-4}$ alkoxy, $C(=O)R_7$, $C_{1-6}$ alkyl, $C_{1-6}$ alkyl substituted optionally with OH, $NR_5R_6$, halogen, $C_{1-4}$ alkoxy, $C(=O)R_7$ or on nitrogen with $NR_5R_6$, $C_{1-4}$ alkoxy, $C(=O)R_7$, $C_{1-6}$ alkyl or $C_{2-6}$ alkyl substituted optionally with OH, $NR_5R_6$, halogen, $C_{1-4}$ alkoxy or $C(=O)R_7$.

$R_3$ is H; halogen; $C_{1-4}$ alkyl; $C_{1-8}$ alkoxy; $C_{1-8}$ alkylthiol; $C_{2-8}$ alkoxy substituted optionally with OH, $NR_5R_6$, halogen, $C_{1-4}$ alkoxy or $C(=)R_7$; $C_{1-4}$ alkyl substituted optionally with $R_4$; or $R_1$ and $R_3$ can be joined together with carbon atoms to form a ring of from 5 to 7 members in which said carbon atoms can be unsubstituted or substituted optionally with $R_4$.

$R_4$ is OH; $C_{1-4}$ alkyl unsubstituted or substituted optionally with OH, $NR_5R_6$, halogen, $C_{1-4}$ alkoxy or $C(=O)R_7$, $C_{1-4}$ alkoxy; $C_{2-4}$ alkoxy substituted optionally with OH, $NR_5R_6$, halogen, $C_{1-4}$ alkoxy or $C(=O)R_7$, $NR_5R_6$; phenyl or $R_{10}$ either of which can be unsubstituted or substituted optionally with OH, $(CH_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0–2 and n is 0–2;

Provided that when G is $SO_2$ and $R_3$ is in the 4 position and is H or halogen then $R_1$ and $R_2$ are not H, $C_{1-6}$ alkyl substituted optionally with OH, $C_{1-6}$ alkoxy, $C_{2-6}$ alkoxycarbonyl, $C_{2-6}$ alkenyl, phenyl, phenoxy, pyridyl, tetrahydrofuryl, $C_{2-6}$ alkanoyl, $C_{2-6}$ alkenyl, nor are they joined to form a 5, 6 or 7 member ring, saturated or unsaturated, comprised of atoms selected optionally from C, O, S, N in which said nitrogen, when saturated, is substituted optionally with H or $C_{1-6}$ alkyl or in which said carbon is substituted optionally with $C_{1-6}$ alkyl, $C_{1-6}$ alkoxy or OH; and when $R_3$ is in the 5 position and is H, Cl, Br, or $C_{1-3}$ alkyl then neither $R_1$ nor $R_2$ can be H or $C_{1-4}$ alkyl; and when G is $C(=O)$ and in the 5-position and $R_3$ is H, then $R_1$ and $R_2$ cannot both be $CH_3$;

$R_5$ & $R_6$ are the same or different and are H; $C_{1-6}$ alkyl; $C_{2-6}$ alkyl substituted optionally with OH, halogen, $C_{1-4}$ alkoxy or $C(=O)R_7$; hydroxy; $C_{1-4}$ alkoxy; $C_{2-4}$ alkoxy substituted optionally with OH, halogen, $C_{1-4}$ alkoxy or $C(=O)R_7$; $C_{3-7}$ alkenyl unsubstituted or substituted optionally with OH, $NR_5R_6$, or $C_{1-4}$ alkoxy; $C_{3-7}$ alkynyl unsubstituted or substituted optionally with OH, $NR_5R_6$, or $C_{1-4}$ alkoxy; $C_{1-2}$alkyl$C_{3-5}$cycloalky; $C(=O)R_7$ or $R_5$ and $R_6$ can be joined to form a ring of 5 or 6 atoms selected from O, S, C or N, such as, pyrrolidine, oxazolidine, thiomorpholine, thiomorpholine 1,1 dioxide, morpholine, piperazine or thiazolidine 1,1-dioxide, which can be unsubstituted or substituted optionally on carbon with OH, (=O), halogen, $C_{1-4}$ alkoxy, $C(=O)R_7$, $C_{1-6}$ alkyl, $C_{1-6}$ alkyl substituted optionally with OH, halogen, $C_{1-4}$ alkoxy, $C(=O)R_7$ or on nitrogen with $C_{1-4}$ alkoxy, $C(=O)R_7$, $S(=O)_mR_8$, $C_{1-6}$ alkyl or $C_{2-6}$ alkyl substituted optionally with OH, $C_{1-4}$ alkoxy, $C(=O)R_7$ or on sulfur by $(=O)_m$, wherein m is 0–2.

$R_7$ is $C_{1-8}$ alkyl; $C_{1-8}$ alkyl substituted optionally with OH, $NR_5R_6$, halogen, $C_{1-4}$ alkoxy or $C(=O)R_9$; $C_{1-4}$ alkoxy; $C_{2-4}$ alkoxy substituted optionally with OH, $NR_5R_6$, halogen or $C_{1-4}$ alkoxy; $NR_5R_6$; or phenyl or $R_{10}$ either of which can be unsubstituted or substituted optionally with OH, halogen, $C_{1-3}$ alkyl, $C_{1-3}$ haloalkoxy, $(CH_2)_nNR_5R_6$, $S(=O)_mR_8$ or $SO_2NR_5R_6$, wherein n is 0 or 1 and m is 0–2.

$R_8$ is $C_{1-4}$ alkyl; $C_{2-4}$ alkyl substituted optionally with OH, $NR_5R_6$, halogen, $C_{1-4}$ alkoxy or $C(=O)R_7$.

$R_9$ is $C_{1-4}$ alkyl; $C_{1-4}$ alkoxy; amino, $C_{1-3}$ alkylamino, or di-$C_{1-3}$ alkylamino; and $R_{10}$ is a monocyclic ring system of 5 or 6 atoms composed of C, N, O, and/or S, such as furan, thiophene, pyrrole, pyrazole, imidazole, triazole, tetrazole, oxazole, isoxazole, isothiazole, thiazole, thiadiazole, pyridine, pyrimidine, pyridazine, and pyrazine.

G is $C(=O)$ or $SO_2$.

In the above definitions, the total number of carbon atoms in a substituent group is indicated by the $C_{i-j}$ prefix where i and j are numbers from 1 to 8 for example. This $C_{i-j}$ definition includes both the straight and branched chain isomers. For example, $C_{1-4}$ alkyl would designate methyl through the butyl isomers; and $C_{1-4}$ alkoxy would designate methoxy through the butoxy isomers.

The term "halogen," either alone or in compound words such as "haloalkyl," means fluorine, chlorine, bromine or iodine. Further, when used in compound words such as "haloalkyl," said alkyl may be partially or fully substituted with halogen atoms, which may be the same or different.

Structure I includes isomers, wherein $R_3$ and $GNR_1R_2$ are attached to the 4 and 5 position respectively or $R_3$ is attached to the 5 position and $GNR_1R_2$ is attached to the 4 position. Many of the novel compounds of Structure I possess one or more chiral centers and this invention includes all enantiomers, diastereomers and mixtures thereof.

In addition to the following teaching, U.S. Pat. Nos. 5,153,192 and 5,240,923, the parents of this case which are commonly a herein by reference, particularly for their synthesis teaching and their many specific examples.

Compounds of the present invention can be prepared using a variety of procedures, a number of which are described below.

Many of the novel compounds of Structure I can be prepared from 5-sulfamoyl-thiophene-2-sulfonyl chlorides or 3-substituted 5-sulfamoyl-thiophene-2-sulfonyl chlorides, or where it is particularly advantageous for subsequent reactions in a specific preparation that the sulfonamide group be protected, 3-substituted 5-(N-t-butylsulfamoyl)-thiophene-2-sulfonyl chlorides can be used. These thiophene-2sulfonyl chlorides can be readily prepared by a variety of procedures known in the art, for example see Gronowitz et al in *Thiophene and its Derivatives*, Vol. 44, Pt. 3, p135. The preparative sequence for novel compounds of Structure I using a protected sulfonamide is illustrated in Equation 1. In general, N-t-butyl-thiophene-2-sulfonamides can be selectively metallated at C5 using a strong organometallic base such as n-butyllithium, subsequent condensation with sulfur dioxide gas produces the intermediate lithium sulfinate salts (Equation 1a). The intermediate sulfinate salt can be readily converted to the corresponding sulfonyl chloride with an appropriate chlorinating agent such as N-chlorosuccinimide; amination of the sulfonyl chloride with a primary alkylamine, primary arylamine, or secondary alkylamine, bearing the desired $R_1$ and $R_2$ substituents, provides, following deprotection, the novel compounds of Structure I (Equation 1b).

In many cases it is more advantageous initially to prepare simplified primary or secondary sulfonamides as described above, but then append the more complex $R_1$ or $R_2$ substituents using standard alkylation reactions (Equation 1c). This sequence can furnish directly certain novel compounds of Structure I; however, subsequent modification of the substituents $R_1$, $R_2$, and $R_3$ can furnish yet other novel compounds of Structure I including novel fused bicyclic compounds; all of which can be prepared using methods known to one skilled in the art. Primary sulfonamides can be prepared from the corresponding sulfonyl chlorides by amination with ammonia or directly from the lithium sulfinate salts using hydroxylamine-O-sulfonic acid (HOSA) (Equation 1d).

Equation 1 a) 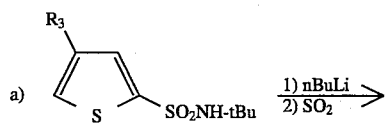

Equation 1 -continued

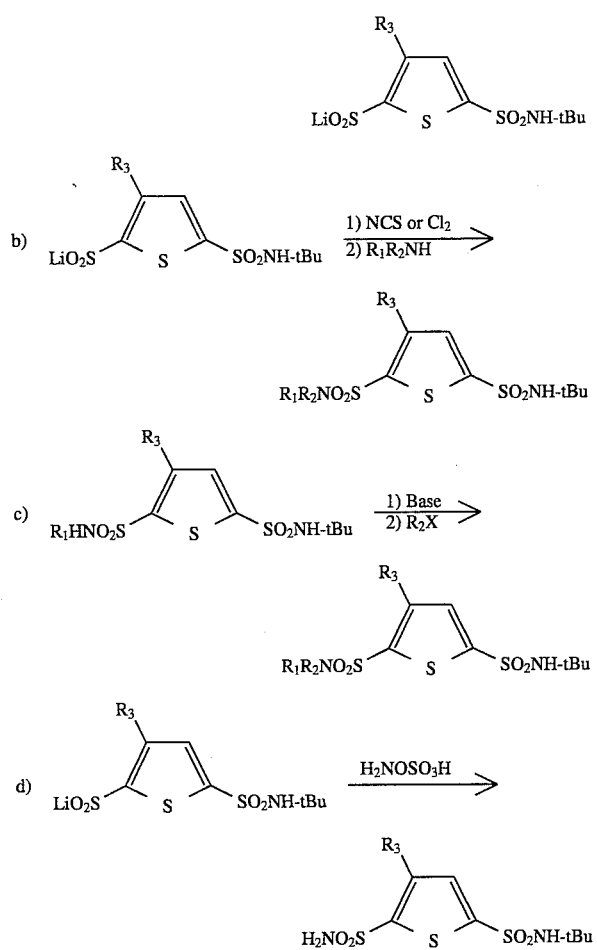

Many of the compounds of Structure I can be prepared using the procedures shown below in Equation 2 or other methods known in the art. Chlorosulfonation of thiophene-2-sulfonamides produces the 4-sulfonyl chlorides (Equation 2a). These intermediate sulfonyl chlorides can be converted to the novel compounds of Structure I using procedures (Equations 2b and 2c) analogous to those described for Equation 1.

Equation 2

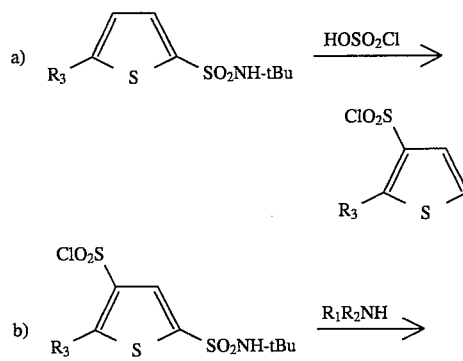

Equation 2 -continued

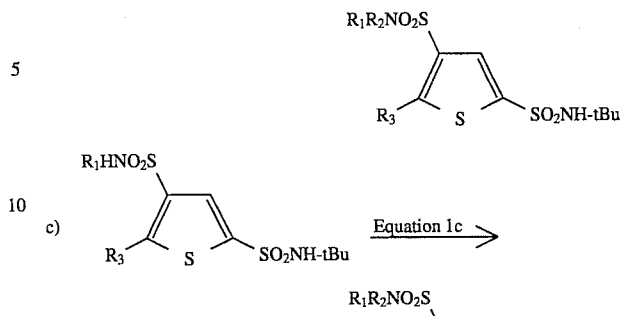

Novel compounds of Structure I wherein $R_1$ and $R_3$ are joined in a manner so as to provide fused bicyclic compounds, such as 3,4-dihydro-thieno-1, 2-thiazine 1,1-dioxides, can be prepared from the appropriately substituted thiophenesulfonamides according to Equations 3–11. Thiophene ketals of Equation 3a, where X is H or halogen, can be readily prepared by standard methods well known to one skilled in the art from commercially available ketones. Treatment of these ketals by the methods of Equations 1a and 1b above provide the intermediate sulfonyl chlorides. The sulfonyl chlorides can be reacted with either ammonia to give the primary sulfonamides, or with the desired alkylamine or arylamine to give a secondary sulfonamides (Equation 3b). Alternately, the primary sulfonamides can be prepared from the intermediate sulfinate salt with hydroxylamine-O-sulfonic acid.

Equation 3

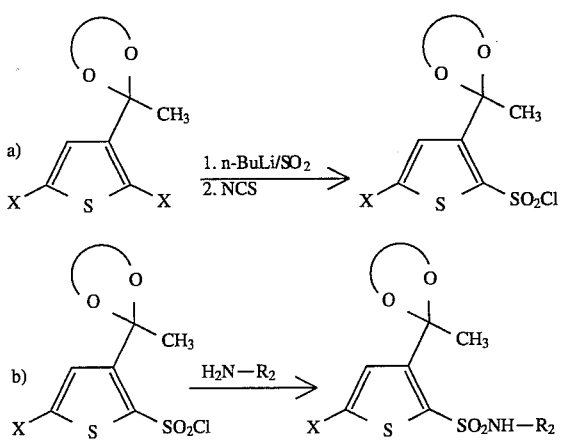

Conversion of these acyclic sulfonamides into the desired thienothiazine compounds can be accomplished using a variety of procedures well known in the art; e.g. acid hydrolysis of the ketal followed by bromination of the ketone and subsequent base catalyzed cyclization of the α-bromoketone (Equation 4).

Equation 4

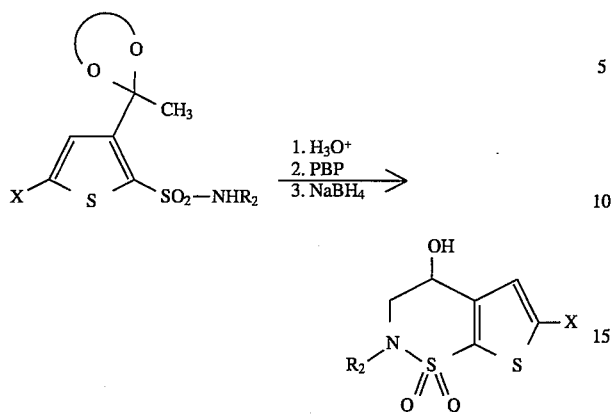

Certain desired bicyclic compounds of Structure I can be readily prepared by a sequence which involves initial alkylation with an appropriate alkyl halide in the presence of a suitable base (Equation 5a) followed by introduction of the sulfamoyl group by procedures analogous to Equations 1a–d, that is metallation of the alkylated product of Equation 4 with a strong organometallic base such as n-butyllithium, followed by treatment with sulfur dioxide to give the intermediate sulfinate salt which is aminated, e.g. by reaction with hydroxylamine-O-sulfonic acid (Equation 5b). Treatment of this intermediate with an appropriate alkyl nitrile in the presence of sulfuric acid provides an amide which upon reduction gives the desired amine [Equation 5c; R' is lower alkyl $(C_{1-4})$].

Equation 5

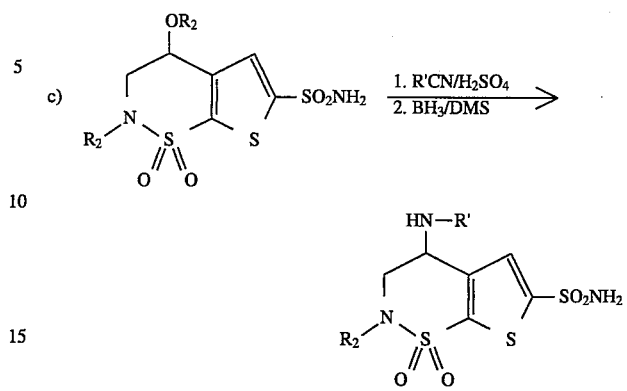

Yet other desirable compounds of Structure I are better prepared according to Equation 6 where the cyclic intermediate from Equation 4 is sulfamoylated (see Equation 5b) at position six (Equation 6a) followed by conversion of the hydroxyl group to a sulfonate ester (e.g. R" is p-toluyl or methyl) and reaction of this intermediate with the desired alkylamine (Equation 6b).

Equation 6

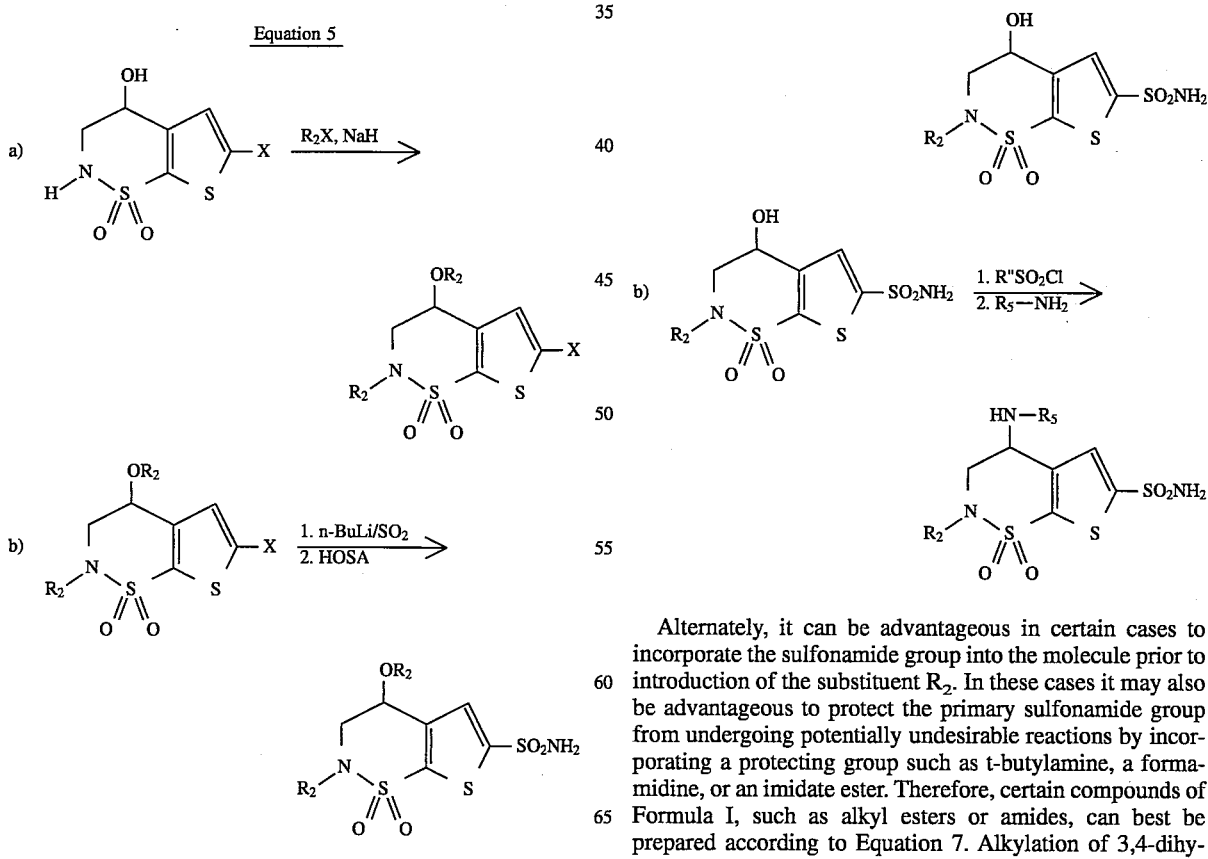

Alternately, it can be advantageous in certain cases to incorporate the sulfonamide group into the molecule prior to introduction of the substituent $R_2$. In these cases it may also be advantageous to protect the primary sulfonamide group from undergoing potentially undesirable reactions by incorporating a protecting group such as t-butylamine, a formamidine, or an imidate ester. Therefore, certain compounds of Formula I, such as alkyl esters or amides, can best be prepared according to Equation 7. Alkylation of 3,4-dihydro-4-hydroxy-N-(1,1-dimethyl)ethyl-2H-thieno[3,2-e]-1, 2-thiazine-6-sulfonamide 1,1-dioxide, which can be prepared as described in U.S. Pat. No. 5,240,923, with, for example, a haloalkylester using conditions similar to Equation 5a or variations known to the art (Equation 7a) followed by amination at position four according to Equation 6b, and subsequent removal of the protecting group, for example, by treatment with an acid such as trifluoroacetic acid where the protecting group is t-butyl (Equation 7c), provides esters of Formula I. Other esters of Formula I can be prepared from an ester so prepared by transesterification using various conditions known to the art (see, *Comprehensive Organic Transformations*, R. C. Larock, page 985). Amination of the alkylesters by a variety of conditions known to the art provides the substituted alkylamides of Formula I (Equation 7d).

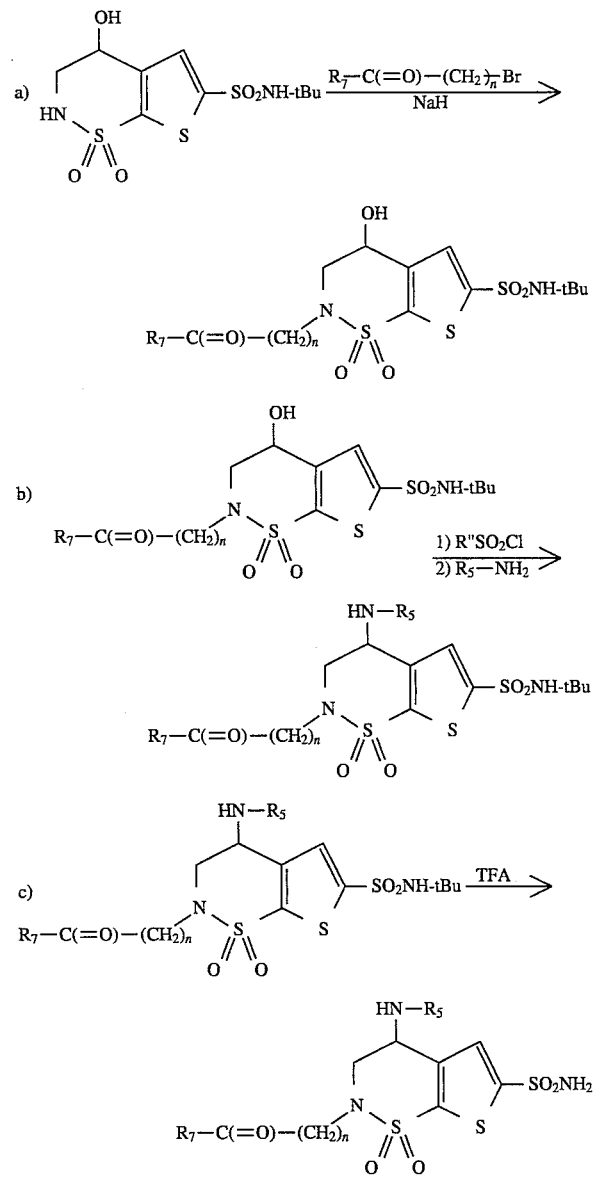

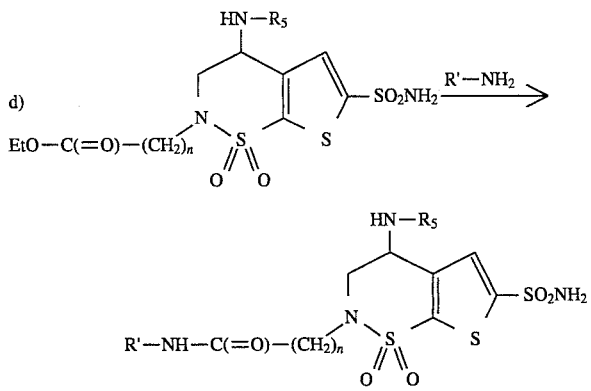

Yet other compounds of Formula I are also most advantageously prepared by modification of an intermediate functionality initially incorporated at position two; acylated hydroxyalkyl or acylated aminoalkyl substituents are examples of such substituents. Treatment of the product of Equation 6, where $R_2$ is an alkoxyalkyl group, under conditions suitable for ether cleavage, for example with a Lewis acid, such as borontribromide or bromodimethylborane, provides the hydroxyalkyl substituent at position two (Equation 8a) which can be selectively acylated by treatment with the desired acyl chloride under acidic conditions, for example in the presence of trifluoroacetic acid, to give compounds of Formula I wherein $R_2$ is an acylated hydroxyalkyl group (Equation 8b).

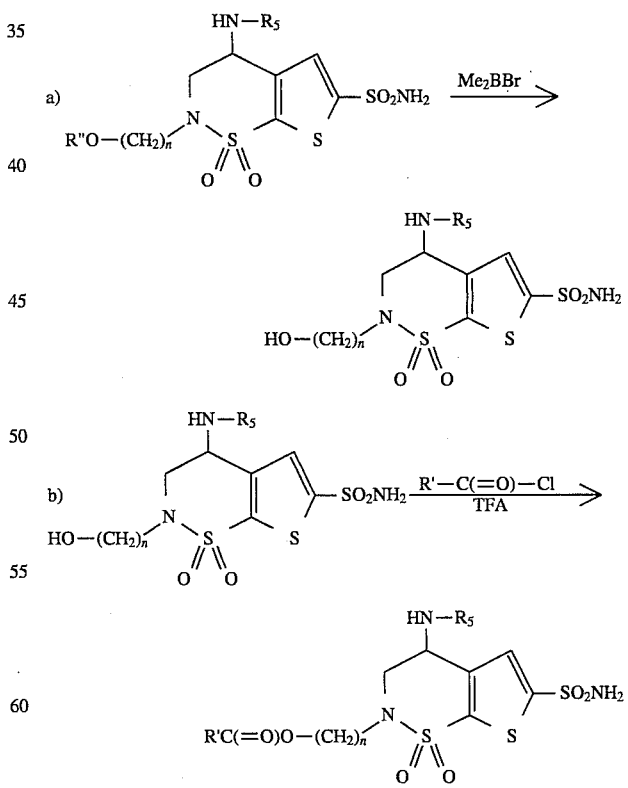

Treatment of the product of Equation 6, where $R_2$ is an alkoxalkyl group, with hydrobromic acid provides ether cleavage with concomitant bromination to give the haloalkyl substituent (Equation 9a) which can be converted to an aminoalkyl substituent by standard conditions known in the art, for example, initial formation of the alkylazide by treatment with sodium azide followed by reduction of the azide to the amine (Equation 9b). Acylation of the amine with the desired acyl chloride or acid anhydride provides compounds of Formula I wherein $R_2$ is an acylated aminoalkyl substituent (Equation 9c).

phine, or by displacement of a sulfonate ester under basic conditions (Equation 10b). The requisite $R_2$ group can be introduced using standard alkylation conditions (Equation 10c) and introduction of the primary sulfonamide can be accomplished by procedures similar to those already described in Equations 1a, 1b, and 1d (Equation 7d).

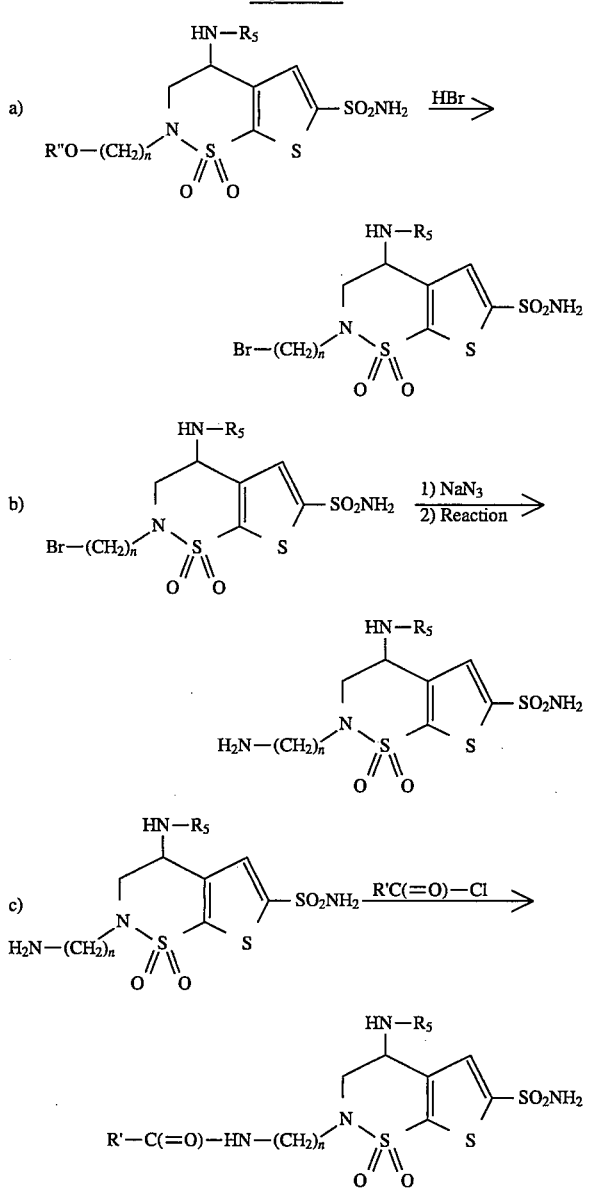

Equation 9

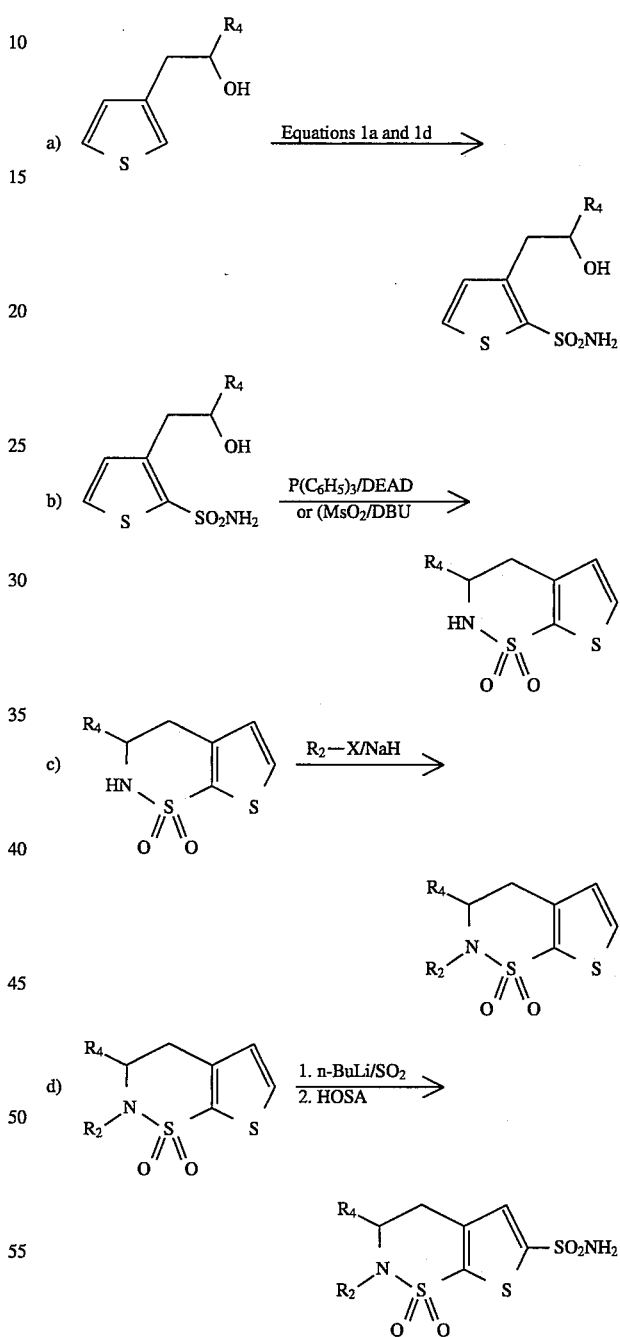

Equation 10

Still other desirable compounds of Structure I can be prepared (Equation 10) from an appropriate thienylethanol; these intermediate alcohols can be readily prepared by procedures well known in the art, e.g. reaction of thienyl-3-acetaldehyde with an appropriate Grignard reagent. Sulfamoylation of such alcohols by the procedures described in Equations 1a and 1d provide exclusively the desired thiophene-2-sulfonamide intermediates of Equation 10a. Cyclization to the desired bicyclic thienothiazine can be accomplished by procedures known in the art, but preferably cyclization is accomplished using conditions of the Mitsunobu reaction, diethyl azodicarboxylate-triphenylphos- Yet other fused bicyclic compounds of Structure I, such as tetrahydrothieno[2,3-b]pyridine-2-sulfonamides, can be prepared in much the same manner as already described in Equations 2–6. Thiophene ketals (see Equation 3a) are readily metallated by strong organometallic bases and upon subsequent reaction with carbon dioxide provide the lithium carboxylates which upon coupling with ammonia or a desirable amine in the presence of a suitable activating agent such as dicyclohexylcarbodiimide, provides the primary or secondary thiophene-2carboxamides, respectively (Equation 11a). Deprotection of the amides followed by bromination provides the α-bromoketones which can be readily cyclized under basic conditions (11b). Introduction of the desirable primary sulfonamide group can be accomplished in a manner analogous to that previously described in Equations 1a, 1b, and 1d. The alcohols can be transformed to amines if desired by initial conversion to an aryl or alkyl sulfonate ester and subsequent treatment with the desired amine (Equation 11c).

shown in Equation 12a. This intermediate primary amine can be selectively transformed to more desirable secondary amines using well known methods of reductive amination, that is treatment with the desired aldehyde and a suitable reducing agent, or reductive alkylation, that is reaction with the requisite carboxylic acid and a suitable reducing agent [Equation 12b; G is H or loweralkyl $(C_{1-4})$]. Introduction of the primary sulfonamide can be accomplished as previously described in Equations 1a, 1b, and 1d, but preferably using t-butyllithium as the base (Equation 12c).

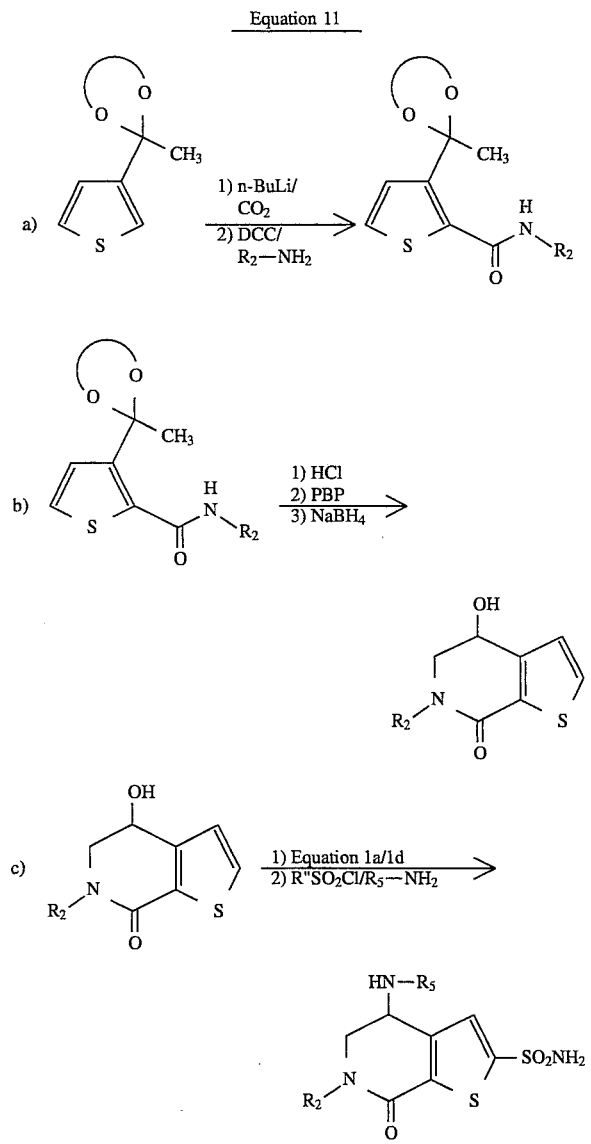

Equation 11

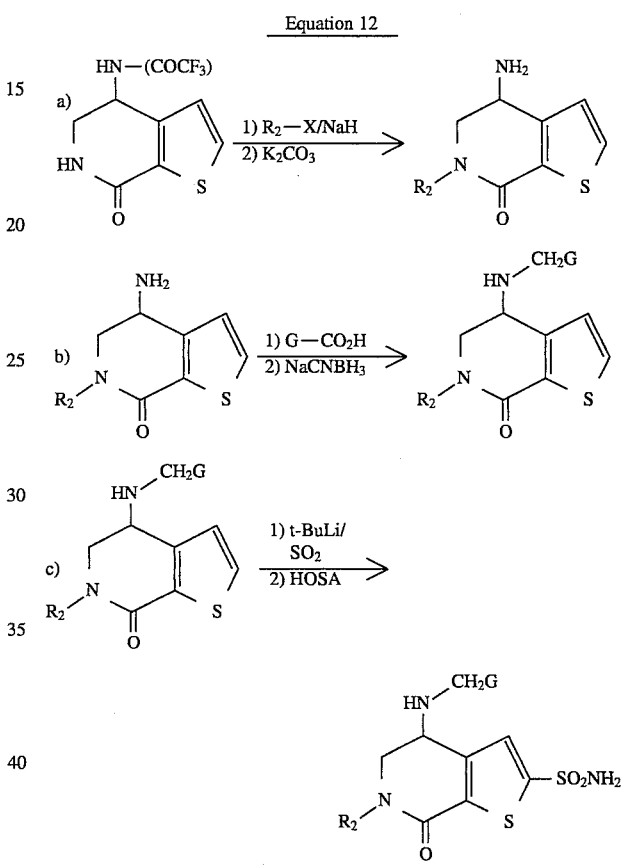

Equation 12

Alternately, such compounds can be prepared by the procedure shown in Equation 12. Alkylation of 4,5,6,7-tetrahydro-4-(trifluoroacetamido)-7-oxo-thieno[2,3b]pyridine [*Heterocycles*, 27, 1637 (1988)] with the requisite $R_2$ group using standard alkylation procedures followed by hydrolysis of the amide provides the primary amine as Certain cyclic compounds of Structure I, such as the 2,3-dihydrothienoisothiazoles, can be obtained through the modification of an existing cyclic compound (Equation 13). The metallated ketals of Equation 3 can be readily converted to the desired intermediate mercaptoketones as shown in Equation 13a, and the oxime O-esters of such compounds can be cyclized according to Equation 5b. Oxidation and subsequent reduction of the thienoisothiazole by procedures well known in the art provides the intermediate cyclic sulfonamides shown in Equation 13c. These cyclic sulfonamides can be substituted on nitrogen utilizing standard alkylation procedures such as demonstrated by Equation 13d. Incorporation of the primary sulfonamide into position five of these examples of Structure I can be accomplished under the basic conditions demonstrated by Equations 1a–d.

Equation 13

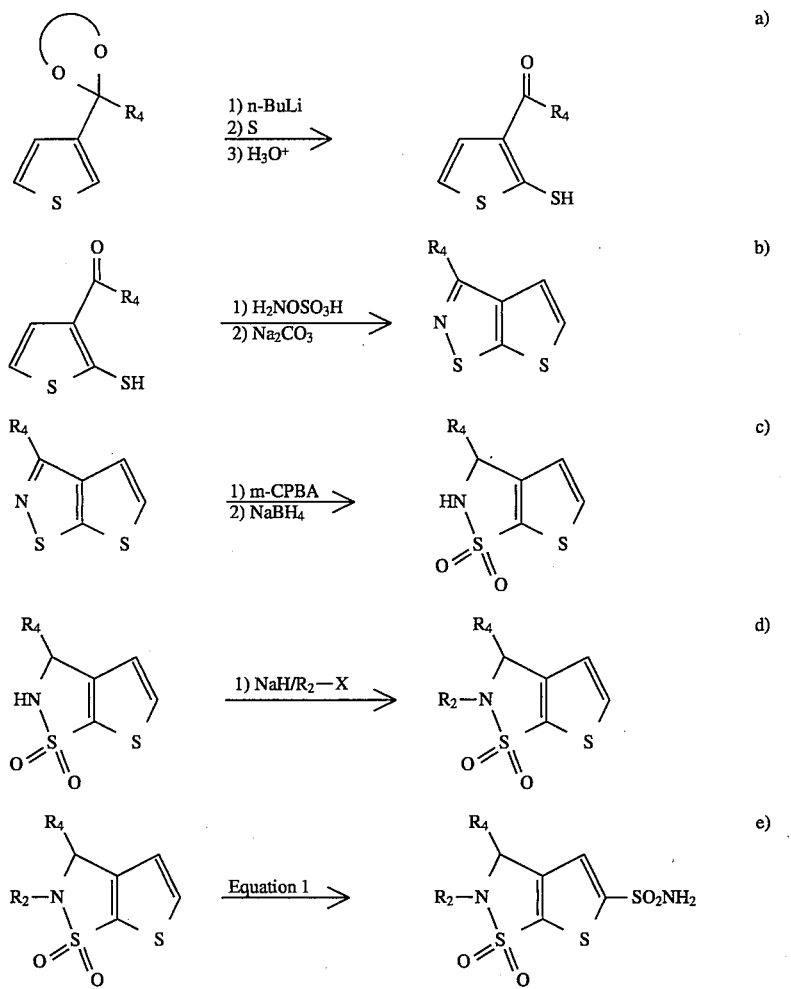

Yet other cyclic compounds of Structure I, such as tetrahydrothienothiazepines, can be prepared from substituted thiophenesulfonamides according to Equation 14. Thiophene acetals can be metallated in the two position with strong metallic bases in a manner similar to that described in Equation 3a for thiophene ketals. These intermediates can be further converted to the thiophene-2-sulfonamides desired for Equation 14a in a manner similar to that described for thiophene ketals by Equations 3a and 1d. Thiophene acetals can be readily converted to the corresponding aldehydes by acid hydrolysis, and reaction of these aldehydes with an olefinic Grignard reagent can provide the olefin intermediates of Equation 14a. The allylic alcohols from Equation 14a can be oxidized to intermediate ketones by a variety of procedures well known to the art, and these ketones can be cyclized upon treatment under basic conditions, such as sodium carbonate, to the cyclic sulfonamides (Equation 14b). The requisite $R_1$ group can be appended by using standard alkylation reactions (Equation 14c) and these intermediates can be reduced to the requisite alcohols with a suitable reagent, such as sodium borohydride. The alcohols can be transformed to amines by initial conversion to an alkyl or aryl sulfonic acid ester, and subsequent treatment of this intermediate with the desired primary or secondary amine (Equation 14d). Introduction of the primary sulfonamide functionality into the tetrahydrothienothiazepines can be accomplished by procedures similar to those already described in Equations 1a, 1b, and 1d (Equation 14e).

Equation 14 a)

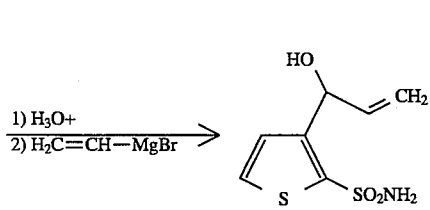

-continued
Equation 14

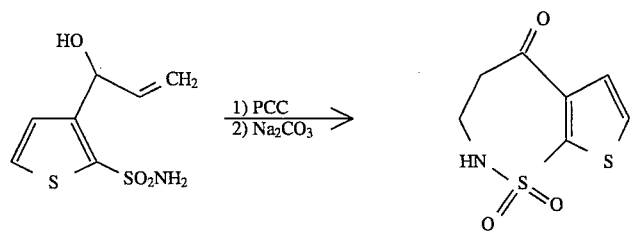
b)

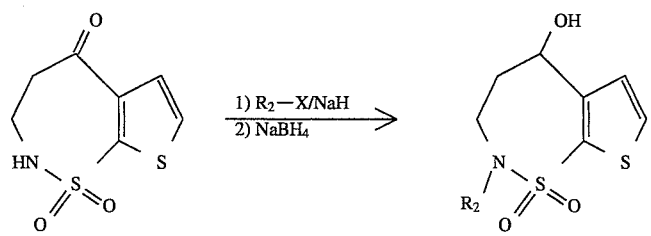
c)

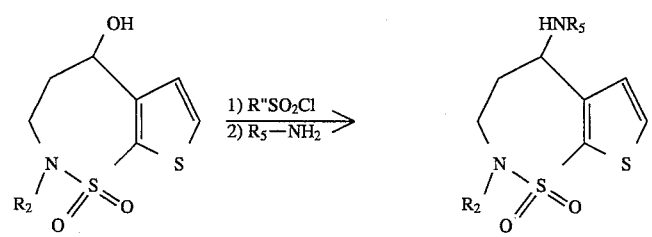
d)

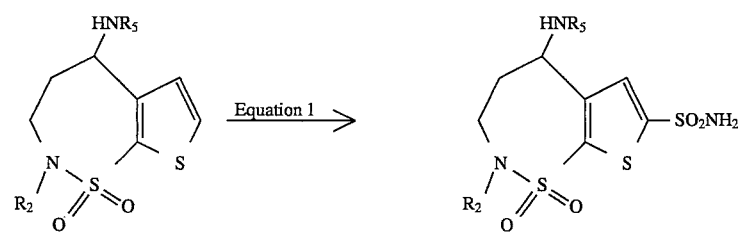
e)

Thienothiazines isomeric to those described in Equations 4–10 can be prepared using a similar route starting from 2,5-dichlorothiophene as shown in Equation 15. Chlorosulfonation of this starting material followed by amination using methods similar to those described in Equation 2 will provide the desired thiophene-3-sulfonamide (Equation 15a). Subsequent treatment of this intermediate with n-butyllithium at low temperature followed by quenching with acetic anhydride will give rise to the ketone of Equation 15b. This key intermediate can then be converted into the desired novel compounds of Structure I using substantially the same general methods described in Equations 4–10.

Equation 15

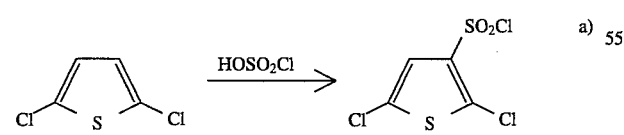
a)

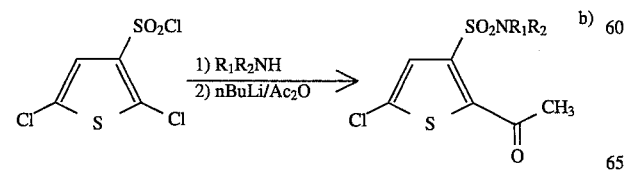
b)

Still other desirable compounds of Structure I, such as 5-sulfamoyl-thiophene-2-carboxamides, can be prepared according to Equation 16. Treatment of the readily prepared 5-bromo-thiophene-2-sulfonamides trader palladium mediated amidation reaction conditions [see for example *J. Org. Chem.*, 39, 3327 (1974)] in the presence of the desired amine component provides the novel compounds of Structure I. Alternately, 5-bromo-thiophene-2-sulfonamides can be initially protected, such as with the formamidine group, followed by treatment with a strong organometallic base, such as n-butyllithium or LDA, and carbon dioxide to give the intermediate carboxylic acid. Treatment of this intermediate acid with an activiating agent, such as dicyclohexylcarbodiimide or triphenylphosphine triflate, followed by reaction with the desired amine component provides, following deprotection, the desired compounds of Structure I.

Equation 16

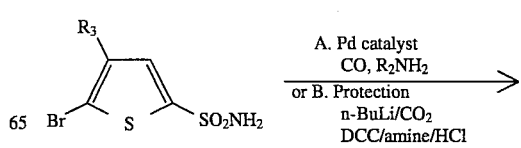

-continued
Equation 16

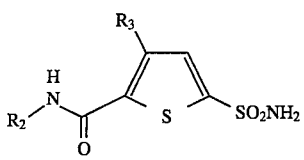

The compounds of Structure I can be incorporated into various types of ophthalmic formulations for delivery to the eye. These compounds may be combined with ophthalmologically acceptable preservatives, surfactants, viscosity enhancers, penetration enhancers, buffers, sodium chloride and water to form an aqueous, sterile ophthalmic suspensions or solutions. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940 or the like according to the published formulations for analogous ophthalmic preparations; preservatives and tonicity agents can be incorporated. Ophthalmic solution formulations may be prepared by dissolving the active ingredient in a physiologically acceptable isotonic aqueous buffer. Further, the ophthalmic solution may include an ophthalmologically acceptable surfactant to assist in dissolving the active ingredient. Furthermore, the ophthalmic solution may contain a thickener such as hydroxymethylcellulose, hydroxyethylcellulose, hydroxypropylmethylcellulose, methylcellulose, polyvinylpyrrolidone, or the like to improve the retention of the medicament in the conjunctival sac.

The compounds are preferably formulated as topical ophthalmic suspensions or solutions, with pH of about 4.5 to 7.8. The compounds will normally be contained in these formulations in an amount of 0.05% to 10% by weight, but preferably in an amount of 0.10% to 2.0% by weight. Thus, for topical presentation 1 to 3 drops of these formulations would be delivered to the surface of the eye 1 to 4 times a day according to the routine discretion of a skilled clinician.

The following examples, which are in no way limiting, illustrate the preparation of selected examples of the novel compounds of Structure I. The compounds set forth in Examples 1, 2, 6, and 9 represent the preferred thiophene sulfonamides of this invention. The compounds represented in Examples 1 and 2 are most preferred.

EXAMPLE 1

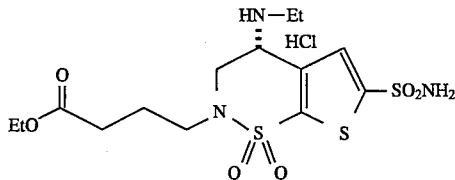

R-(+)-6-(Aminosulfonyl)-4-ethylamino-3,4-dihydro-2H-thieno[3,2-e]-1,2-thiazine-2-butanoic acid 1,1-dioxide ethyl ester hydrochloride Step A: 2,3-Dihydro-N-(1,1-dimethylethyl)-4-oxo-4H-thieno[3,2-e]-1,2-thiazine-6-sulfonamide 1,1-dioxide To a solution of 3,4-dihydro-4-hydroxy-N-(1,1-dimethylethyl)-2H-thieno[3,2-e]-1,2-thiazine-6-sulfonamide 1,1-dioxide (3.36 g, 9.87 mmol) in acetone (15 mL) at room temperature was added Jones reagent [2 mL (prepared by dissolving $CrO_3$ (7 g) in $H_2O$ (50 mL) and adding $H_2SO_4$ (6.1 mL)]. The mixture was stirred at room temperature for one hour, solvent was evaporated and the residue dissolved in ethyl acetate (75 mL). This solution was washed with saturated aqueous sodium bicarbonate until the the organic layer was neutral. The aqueous layer was separated and washed with ethyl acetate (3'25 mL). The combined extracts were dried ($NaSO_4$) and evaporated to provide a residue which was purified by column chromatography (silica, 40% ethyl acetate in hexane) to give an off-white solid (2.74 g, 82%): mp 170°–172° C.

Step B: (S)-N-(1,1-dimethylethyl)-3,4-dihydro-4-hydroxy-2H-thieno[3,2-e]-1,2-thiazine-6-sulfonamide 1,1-dioxide A solution of (+)-diisopinocamphenylchloroborane (3.8 g, 11.8 mmol) was dissolved in anhydrous THF (10 mL) under nitrogen and cooled to −35° C.; the product from Step A (0.8 g, 2.36 mmol) was added and this mixture was stirred at −35° C. for 24 hr. The solvent was evaporated and the residue was mixed with diethyl ether (15 mL) and diethanol amine (0.62 g, 5.9 mmol) was added followed by stirring for 2 h, filtration, and evaporation. The residue was purified by column chromatography (silica, hexane then hexane/ethyl acetate gradient) to give a colorless solid (0.60 g, 75%): mp 57°–58° C. The optical purity was established to be >90% ee by HPLC analysis of the diastereomeric esters formed with (S)-α-methoxyphenylacetic acid.

Step C: (S)-6-[[(1,1-dimethylethyl)amino]sulfonyl]-3,4-dihydro-4-hydroxy-2H-thieno[3,2-e]-1,2-thiazine-2-butanoic acid 1,1-dioxide ethyl ester hydrochloride A solution of (S)-N-(1,1-dimethylethyl)-3,4-dihydro-4-hydroxy-2H-thieno[3,2-e]-1,2-thiazine-6-sulfonamide 1,1-dioxide (10.62 g, 33.23 mmol) in DMF (120 ml) was cooled to 0° C. and sodium hydride (2.62g, 65 mmol of a 60% suspension in mineral oil) was added. The mixture was stirred for 20 minutes and then ethyl 4-bromobutyrate (6.70 mL, 46.85 mmol) was added. After stirring at room temperature for 6 hr, the DMF was evaporated to give a residue which was diluted with aqueous 1N HCl. This mixture was extracted with ethyl acetate (3×100 mL) and the combined extracts were dried ($MgSO_4$) and evaporated to provide an oil which was purified by column chromatography (silica, hexane-ethyl acetate gradient) to give the desired compound as an oil (13.35 g, 92%); this product was used in subsequent reactions.

Step D: (R)-6-[[(1,1-dimethylethyl)amino]sulfonyl]-4-ethylamino-3,4-dihydro-2H-thieno[3,2-e]-1,2-thiazine-2-butanoic acid 1,1-dioxide ethyl ester The product of Step A (8.50g, 19.07 mmol) was dissolved in THF (130 mL) and cooled to 0° C. Triethylamine (10.69 mL, 76.28 mmol) was added followed by p-toluenesulfonyl chloride. The mixture was stirred for three hours and an aqueous solution of ethylamine (20 mL) was added. The mixture was stirred overnight at room temperature and then evaporated to a residue which was diluted with ethyl acetate (100 mL). The ethyl acetate was separated, dried ($MgSO_4$) and evaporated to provide a brown residue which was purified by column chromatography (silica, hexane-ethyl acetate gradient) to give 3.5 g (37.6%) of the desired compound as an oil.

Step E: R-(+)-6-(Aminosulfonyl)-4-ethylamino-3,4-dihydro-2H-thieno[3,2-e]-1,2-thiazine-2-butanoic acid 1,1-dioxide ethyl ester hydrochloride The product from Step B (3.5g, 7.27 mmol) was dissolved in trifluoroacetic acid (20 mL) and stirred for 18 h at room temperature. Evaporation of trifluoroacetic acid provided an oily residue which was dissolved in ethyl acetate to which was added a saturated aqueous solution of sodium bicarbonate. The ethyl acetate layer was separated, dried (MgSO₄) and evaporated to a residue which was chromatographed (silica, hexane-ethyl acetate gradient) to give an oil (2.16 g, 70%). This oil was dissolved in ether (50 mL) and a 1N solution of HCl in ether was added. The precipitate was collected and crystallized from ethyl acetate; mp 100°–102° C.; $[\alpha]_D=+20°$ (c=0.50, MeOH); ee >98% by HPLC. Analysis. Calculated for $C_{14}H_{24}N_3O_6S_3Cl\cdot1H_2O$: C, 35.03; H, 5.46; N, 8.75. Found: C, 35.13; H, 5.40; N, 8.75.

EXAMPLE 2

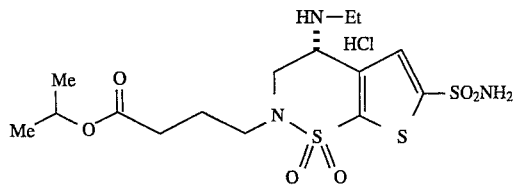

R-(+)-6-(Aminosulfonyl)-4-ethylamino-3,4-dihydro-2H-thieno[3,2-e]-1,2-thiazine-2-butanoic acid 1,1-dioxide 1-methylethyl ester hydrochloride By following the procedure described in Example 1 but using 4-bromobutanoic acid 1-methylethyl ester instead of 4-bromobutanoic acid ethyl ester in Step A, the desired compound was prepared: mp 161°–163° C.; $[\alpha]_D=+17.78°$(c=0.50, MeOH); ee >98% by HPLC. Analysis. Calculated for $C_{15}H_{26}N_3O_6S_3Cl$: C, 37.85; H, 5.50; N, 8.83. Found: C, 37.88; H, 5.46; N, 8.79.

EXAMPLE 3

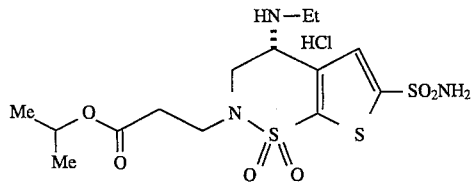

R-(+)-6-(Aminosulfonyl)-4-ethylamino-3,4-dihydro-2H-thieno[3,2-e]-1,2-thiazine-2-propanoic acid 1,1-dioxide 1-methylethyl ester hydrochloride By following the procedure described in Example 1 but using 3-bromopropanoic acid 1-methylethyl ester instead of 4-bromobutanoic acid ethyl ester in Step A, the desired compound was prepared: mp 213°–215° C. $[\alpha]_D=+15.4°$(c=0.5, MeOH); ee >98% by HPLC. Analysis. Calculated for $C_{14}H_{24}N_3O_6S_3Cl$: C, 36.39; H, 5.23; N, 9.10. Found. C, 36.66; H, 5.32; N, 9.08.

By using modifications of the above procedures but replacing ethylamine where required with the appropriate alkylamine in Step D and using the appropriate haloalkyl ester in Step C, the following compounds can be prepared:
1. (R)-6-(Aminosulfonyl)-3,4-dihydro-4-propylamino-2H-thieno[3,2-e]-1,2-thiazine-2-butanoic acid 1,1-dioxide 1-methylethyl ester
2. (R)-6-(Aminosulfonyl)-4-ethylamino-3,4-dihydro-2H-thieno[3,2-e]-1,2-thiazine-2-butanoic acid 1,1-dioxide 1,1-dimethylethyl ester
3. (R)-6-(Aminosulfonyl)-4-[(2-methylpropyl)amino]-3,4-dihydro-2H-thieno[3,2-e]-1,2-thiazine-2-butanoic acid 1,1-dioxide 1-methylethyl ester
4. (R)-6-(Aminosulfonyl)4-[(cyclopropylmethyl)amino]-3,4-dihydro-2H-thieno[3,2-e]-1,2-thiazine-2-butanoic acid 1,1-dioxide ethyl ester

EXAMPLE 4

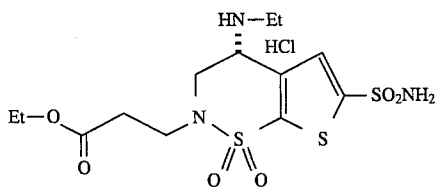

R-(+)-6-(Aminosulfonyl)-4-ethylamino-3,4-dihydro-2H-thieno[3,2-e]-1,2-thiazine-2-propanoic acid 1,1-dioxide ethyl ester hydrochloride To a solution of the product from Example 3 (500 mg, 1.10 mmol) in ethanol (50 mL) was added titanium(IV)isopropoxide (2 mL). The mixture was stirred at reflux temperature for 12 hr, cooled to room temperature, and quenched with Rochelle salt. The precipitated solid was removed by filtration, washed with ethyl acetate, and the filtrate evaporated to provide an oil which was purified by column chromatography (silica, 80% ethyl acetate-hexane). Treatment of an ether solution of the oil with a 1N solution of HCl in ether provided the hydrochloride salt: mp=218°–220° C.; $[\alpha]_D=+6.2°$(c=0.50, MeOH), ee>98% by HPLC. Analysis. Calculated for $C_{13}H_{22}N_3O_6S_3C$;: C, 34.85; H, 4.95; N, 9.37. Found: C, 34.79; H, 5.01; N, 9.33.

By using the product from Example 1 and replacing ethanol with either 2-morpholinylethanol or 2-methoxyethanol the following compounds can be prepared:
1. (R)-6-(Aminosulfonyl)-4-ethylamino-3,4-dihydro-2H-thieno[3,2-e]-1,2-thiazine-2butanic acid 1,1-dioxide 2-morpholinylethyl ester
2. (R)-6-(Aminosulfonyl)-4-ethylamino-3,4-dihydro-2H-thieno[3,2-e]-1,2-thiazine-2acid 1,1-dioxide 2-methoxyethyl ester

EXAMPLE 5

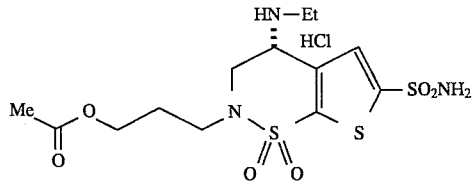

R-(+)-4-Ethylamino-3,4-dihydro-2-(3-acetyloxypropyl)-2H-thieno[3,2-e]-1,2-thiazine-6-sulfonamide 1,1-dioxide hydrochloride Step A. (R)-4-Ethylamino-3,4-dihydro-2-(3-hydroxypropyl)-2H-thieno[3,2-e]-1,2-thiazine-6-sulfonamide 1,1-dioxide To a stirred solution of R-(+)-4-Ethylamino-3,4-dihydro-2-(3-methoxypropyl)-2H-thieno[3,2-e]-1,2-thiazine-6-sulfonamide 1,1-dioxide hydrochloride (7.30 g, 17.0 mmol) in 1,2-dichloroethane (50 mL) was added triethylamine (240 mL, 1.7 mmol) followed by bromodimethylborane (6.78 mL, 69.0 mmol) at 0° C. After 4 h at room temperature, the reaction was quenched by adding a saturated aqueous solution of sodium bicarbonate; this mixture was extracted with ethyl acetate (4×50 mL). The combined extracts were washed with brine (20 mL), dried (MgSO$_4$) and evaporated to give the desired alcohol product as a syrup (6.9 g, 100%).

Step B. R-(+)-2-(3-Acetyloxypropyl)-4-Ethylamino-3,4-dihydro-2H-thieno[3,2-e]-1,2-thiazine-6-sulfonamide 1,1-dioxide hydrochloride To a stirred solution of the product from Step A (1.20 g, 3.30 mmol) in trifluoroacetic acid (10 mL) at room temperature was added acetyl chloride (0.45 mL, 6.50 mmol). After 0.25 hr, trifluoroacetic acid was evaporated under reduced pressure and the residue was dissolved in a saturated aqueous solution of sodium bicarbonate (30 mL). This mixture was extracted with ethyl acetate (3×50.0 mL) and the combined extracts were washed with brine (10 mL), dried (MgSO$_4$) and evaporated to an oil which was purified by column chromatography (silica, 40–80% ethyl acetate-hexane gradient) to yield an oil (1.20 g, 89%). The oil was dissolved in ethanol (5.0 mL) and this solution was treated with ethanolic HCl. Evaporation provided a solid residue which was recrystallized from 2-propanol to give the desired ester (0.60 g, 45%): m.p. 130°–132° C.; [α]$_D$=+16.98° (c=0.63, MeOH); ee>99% determined by chiral HPLC column. Analysis. Calculated for C$_{13}$H$_{22}$ClN$_3$O$_6$S$_3$–0.2 H$_2$O: C, 33.50; H, 5.19; N, 9.02. Found: C, 33.50; H, 5.19; N, 8.96.

EXAMPLE 6

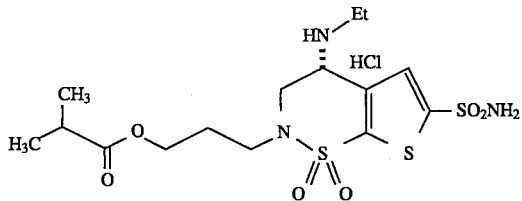

R-(+)-4-Ethylamino-3,4-dihydro-2-[3-(2-methyl-1-oxo-propoxy)propyl]-2H-thieno[3,2-e]-1,2-thiazine-6-sulfonamide 1,1-dioxide hydrochloride To a stirred solution of the product from Example 5, Step A (1.40 g, 3.80 mmol) in trifluoroacetic acid (10.0 mL) at room temperature was added 2-methyl-propanoyl chloride (0.80 mL, 7.60 mmol). After 0.25 hr, trifluoroacetic acid was evaporated under reduced pressure and the residue was added a saturated aqueous solution of sodium bicarbonate (30 mL). This mixture was extracted with ethyl acetate (3×50 mL) and the combined extracts were washed with brine (10 mL), dried (MgSO$_4$) and evaporated to an oil which was purified by column chromatography (silica, 40–80% ethyl acetate-hexane gradient) to yield an oil (1.20 g, 75%). An ethanol (5 mL) solution of this oil was treated with ethanolic HCl. Evaporation provided a solid residue which was recrystallized front methanol/methylene chloride to give the desired ester (0.80 g, 58%): m.p. 210°–211° C.; [α]$_D$=+15.49°(c=0.51, MeOH); ee>99% determined by chiral HPLC column. Analysis. Calculated for C$_{15}$H$_{26}$ClN$_3$O$_6$S$_3$–0.2 H$_2$O: C, 37.56; H, 5.55; N, 8.76. Found: C, 37.25; H, 5.43; N, 8.73.

By using modifications of the above procedure but replacing 2-methylpropanoyl chloride with the appropriate activated carboxylic acid, preferably an acid halide, the following compounds can be prepared:

1. (R)-4-Ethylamino-3,4-dihydro-2-[3-[2-(4-morpholinyl)-1-oxo-ethoxy]propyl]-2H-thieno[3,2-e]-1,2-thiazine-6-sulfonamide 1,1-dioxide
2. (R)-4-Ethylamino-3,4-dihydro-2-[3-[3-(4-morpholinyl)-1-oxo-propoxy]propyl]-2H-thieno[3,2-e]-1,2-thiazine-6-sulfonamide 1,1-dioxide

EXAMPLE 7

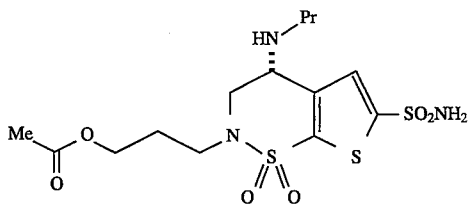

R-(+)-2-(3-acetyloxypropyl)-3,4-dihydro-4-propylamino-2H-thieno[3,2-e]-1,2-thiazine-6-sulfonamide 1,1-dioxide Step A: (R)-3,4-dihydro-2-(3-hydroxypropyl)-4-propylamino-2H-thieno[3,2-e]-1,2-thiazine-6-sulfonamide 1,1-dioxide A solution of (R)-2-[3-(1,1-dimethylethoxy)propyl]-3A-dihydro-4-propylamino-2H-thieno[3,2-e]-1,2-thiazine-6-sulfonamide 1,1-dioxide (0.73 g, 1.66 mmol) in trifluoroacetic acid (20.0 mL) at room temperature was stirred for 20 h. The trifluoroacetic acid was evaporated in vacuo and a saturated solution of sodium bicarbonate (10 L) was added to the residue; this mixture was extracted with ethyl acetate (4×50 mL). The combined extracts were washed with brine (10 mL), dried (MgSO$_4$) and evaporated to a residue which was purified by column chromatography (silica, 50% ethyl acetate-hexane to ethyl acetate) to yield an oil (0.60 g, 94%). The oil was dissolved in ethanol and treated with ethanolic HCl. Recrystallization from 2-propanol gave the hydrochloride salt of the desired alcohol (0.45 g): m.p. 235°–237° C.; [α]$_D$=+18.85°(c=0.52, MeOH); ee>98% determined by chiral HPLC column. Analysis. Calculated for C$_2$H$_{22}$ClN$_3$O$_5$S$_3$: C, 34.32; H, 5.28; N, 10.01. Found: C, 34.60; H, 5.34; N, 9.77.

Step B: R-(+)-2-(3-acetyloxypropyl)-3,4-dihydro-4-propylamino-2H-thieno[3,2-e]-1,2-thiazine-6-sulfonamide 1,1-dioxide To a stirred solution of the product from Step A (0.80 g, 2.09 mmol) in trifluoroacetic acid (10 mL) was added acetyl chloride (0.30 mL, 4.17 mmol) at room temperature. After 0.25 hr, trifluoroacetic acid was evaporated under reduced pressure and the residue was added to a saturated aqueous solution of sodium bicarbonate (30 mL). This mixture was extracted with ethyl acetate (3×50 mL) and the combined extracts were washed with brine (10 mL), dried (MgSO$_4$) and evaporated. The crude residue was purified by column chromatography (silica, 40–80% ethyl acetate-hexane, gradient) to yield a syrup (0.60 g, 67%) which was crystallized from ethyl acetate to give the desired ester (0.60 g, 45%): m.p. 135°–137° C.; [α]$_D$=+14.02°(c=0.49, MeOH); ee>98% determined by chiral HPLC column. Analysis. Calculated for C$_{14}$H$_{23}$N$_3$O$_3$: C, 39.52; H, 5.45; N, 9.87. Found: C, 39.27; H, 5.40; N, 9.63.

EXAMPLE 8

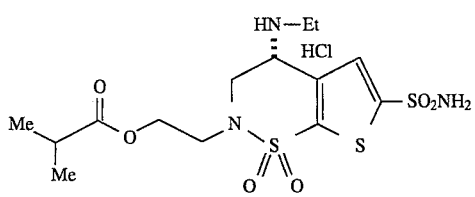

R-(+)-4-Ethylamino-3,4-dihydro-2-[2-(2-methyl-1-oxo-propoxy)ethyl]-2H-thieno[3,2-e]-1,2-thiazine-6-sulfonamide 1,1-dioxide hydrochloride Step A: (R)-4-Ethylamino-3,4-dihydro-2-(2-hydroxyethyl)-2H-thieno[3,2-e]-1,2-thiazine-6-sulfonamide 1,1-dioxide To a stirred solution of (R)-(+)-4-Ethylamino-3,4-dihydro-2-(2-methoxyethyl)-2H-thieno[3,2-e]-1,2-thiazine-6-sulfonamide 1,1-dioxide hydrochloride (6.03 g, 15.0 mmol) in 1,2-dichloroethane (50 mL) was added triethylamine (210 mL, 1.5 mmol) followed by bromodimethylborane (5.79 mL, 59.0 mmol) at 0° C. After 4 h at room temperature, the reaction was quenched by adding a saturated aqueous solution of sodium bicarbonate; this mixture was extracted with ethyl acetate (4×50 mL). The combined extracts were washed with brine (20 mL), dried (MgSO$_4$) and evaporated to give the desired alcohol product as a syrup (4.8 g, 91%).

Step B: R-(+)-4-Ethylamino-3,4-dihydro-2-[2-(2-methyl-1-oxo-propoxy)ethyl]-2H-thieno[3,2-e]-1,2-thiazine-6-sulfonamide 1,1-dioxide hydrochloride To a stirred solution of the product from Step A (0.99 g, 2.82 mmol) in trifluoroacetic acid (10.0 mL) at room temperature was added 2-methylpropanoyl chloride (0.45 mL, 6.50 mmol). After 0.25 hr, trifluoroacetic acid was evaporated under reduced pressure and the residue was dissolved in a saturated aqueous solution of sodium bicarbonate (30.0 mL). This mixture was extracted with ethyl acetate (3×70 mL) and the combined extracts were washed with brine (10 mL), dried (MgSO$_4$) and evaporated to an oil which was purified by column chromatography (silica, 30 to 50% ethyl acetate-hexane gradient) to yield an oil. The oil was dissolved in ethanol (5.0 mL) and this solution was treated with ethanolic HCl. Evaporation provided a solid residue which was recrystallized from ethanol/ethyl acetate to give the desired ester (0.54 g): m.p. 213°–214° C.; $[\alpha]_D$18.94°(c= 0.57, MeOH); ee>99% determined by chiral HPLC column. Analysis. Calculated for $C_{13}H_{22}ClN_3O_6S_3$: C, 36.40; H, 5.24; N, 9.10. Found: C, 36.17; H, 5.18; N, 8.96.

By following the above procedure but replacing 2-methylpropanoyl chloride with either acetyl chloride or cyclopropanecarbonyl chloride in Step B the following compounds were prepared:

1. R-(+)-4-Ethylamino-3,4-dihydro-2-(2-acetyloxyethyl)-2H-thieno[3,2-e]-1,2-thiazine-6-sulfonamide 1,1-dioxide hydrochloride, mp 155°–156° C.
2. R-(+)-2-[6-(Aminosulfonyl)-4-ethylamino-3,4-dihydro-2H-thieno[3,2-e]-1,2-thiazine-2-yl]ethyl cyclopropanecarboxylate $S^1,S^1$-dioxide hydrochloride, mp 218°–220° C.

By using modifications of the above procedure but replacing 2-methylpropanoyl chloride with the appropriate activated carboxylic acid, preferably an acid halide, the following compounds can be prepared:

3. (R)-4-Ethylamino-3,4-dihydro-2-[4-methoxyphenylcarbonyloxy)propyl]-2H-thieno[3,2-e]-1,2-thiazine-6-sulfonamide 1,1-dioxide
4. (R)-4-Ethylamino-3,4-dihydro-2-[(3-methoxyloxo-propoxy)ethyl]-2H-thieno[3,2-e]-2-thiazine-6-sulfonamide1,1-dioxide
5. (R)-4-Ethylamino-3,4-dihydro-2-[(3-hydoxy-1-oxo-propoxy)ethyl]-2H-thieno[3,2-e]-1,2-thiazine-6-sulfonamide 1,1-dioxide

EXAMPLE 9

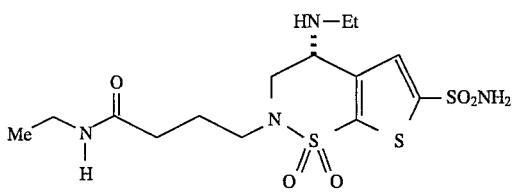

R-(+)-6-(Aminosulfonyl)-N-ethyl-4-ethylamino-3,4-dihydro-2H-thieno[3,2-e]-1,2-thiazine-2-butanamide 1,1-dioxide The product from Example 1, Step C (0.60 g, 1.3 mmol) was dissolved in an aqueous solution of ethylamine and the mixture was stirred at room temperature for 72 h. The reaction mixture was evaporated to a residue which was purified by column chromatography (silica, 2% methanol in ethyl acetate) to give a solid (0.30 g). Recrystallization from ethyl acetate/hexane provided the desired amide: mp 162°–164° C.; $[\alpha]_D$=+12.9°(c=0.50, MeOH); ee>98% determined by chiral HPLC column. Analysis. Calculated for $C_{14}H_{24}N_4O_5S_3$: C, 39.60; H, 5.70; N, 13.20. Found. C, 39.61; H, 5.73; N, 13.10.

By following the above procedure but using instead the ester prepared in Example 4 the following compound was prepared:

1. R-(+)-6-(Aminosulfonyl)-N-ethyl-4-ethylamino-3,4-dihydro-2H-thieno[3,2-e]-1,2-thiazine-2-propanamide 1,1-dioxide hydrochloride, mp 203°–205° C.

By using modifications of the above procedure but replacing the ethyl ester with an activated ester when appropriate and replacing ethylamine with the appropriate alkylamine, the following compounds can be prepared.

2. (R)-6-(Aminosulfonyl)-N-(2-methoxyethyl)-4-ethylamino-3,4-dihydro-2H-thieno[3,2-e]-1,2-thiazine-2-propanamide 1,1-dioxide
3. (R)-6-(Aminosulfonyl)-N-methyl-4-ethylamino-3,4-dihydro-2H-thieno[3,2-e]-1,2-thiazine-2-propanamide 1,1-dioxide
4. (R)-6-(Aminosulfonyl)-N-cyclopropyl-4-ethylamino-3,4-dihydro-2H-thieno[3,2-e]1,2-thiazine-2-propanamide 1,1-dioxide
5. (R)-N-[[[6-(Aminosulfonyl)-4-ethylamino-3,4-dihydro-2H-thieno[3,2-e]-1,2-thiazin-2-yl]ethyl]carbonyl]alanine ethyl ester $S^1,S^1$-dioxide

EXAMPLE 10

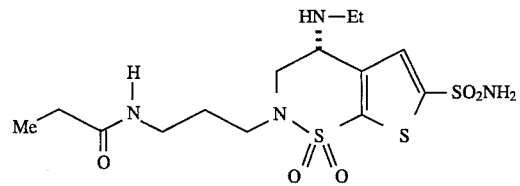

(R)-N-[[6-(Aminosulfonyl)-4-ethylamino-3,4-dihydro-2H-thieno[3,2-e]-1,2-thiazin-2-yl]propyl]propanamide $S^1,S^1$-dioxide Step A: (R)-2-(3-Bromopropyl)-4-ethylamino-3,4-dihydro-2H-thieno[3,2-e]-1,2-thiazine-6-sulfonamide 1,1-dioxide hydrobromide A solution of R-(+)-4-Ethylamino-3,4-dihydro-2-(3-methoxypropyl)-2H-thieno[3,2-e]-1,2-thiazine-6-sulfonamide 1,1-dioxide hydrochloride (4.5 g, 110.7 mmol) in 48% hydrobromic acid (20 mL) was heated at 80° C. for 72 h. The reaction mixture was evaporated to give a pale tan solid (4.8 g, 96%) which was used in subsequent reactions without further purification.

Step B: (R)-2-(3-Azidopropyl)-4-ethylamino-3,4-dihydro-2H-thieno[3,2-thiazine-6-sulfonamide 1,1-dioxide To a solution of the product from Step A (0.46 g, 0.90 mmol) in DMF (3 mL) at room temperature was added sodium azide (0.30 g, 4.49 mmol) and this mixture was stirred for 16 h. Water was added and the mixture extracted with ethyl acetate (3×100 mL). The combined extracts were washed with brine, dried ($MgSO_4$), and evaporated to a residue which was chromatographed (silica, 50% to 70% ethyl acetate in hexane gradient) to give the desired azide as an oil; this material was used in the subsequent reaction without further purification. Step C: (R)-2-(3-Aminopropyl)-4-ethylamino-3,4-dihydro-2H-thieno[3,2-e]-1,2-thiazine-6-sulfonamide 1,1-dioxide A solution of the product from Step B (2.2 g, 6.0 mmol) in THF (10 mL) is combined with water (162 mL) and triphenylphosphine (1.47 g, 6.0 mmol); this mixture is stirred at room temperature for 8 h, or until the reaction is complete as determined by thin layer chromatography. Additional water is added and the reaction mixture is extracted with ethyl acetate (3×50 mL). The combined extracts are combined and washed with brine, dried ($MgSO_4$), and evaporated to a residue which can be purified by column chromatography (silica) to give the desired amine.

Step D: (R)-N-[[6-(Aminosulfonyl)-4-ethylamino-3,4-dihydro-2H-thieno[3,2-e]-1,2-thiazin-2-yl]propyl]propanamide $S^1,S^1$-dioxide A solution of the product from Step C (0.90 g, 3.36 mmol) in ethyl acetate (5 mL) is combined with propanoyl chloride (0.3 mL, 3.36 mmol) at 0° C. After tlc has demonstrated the reaction to be complete, approximately 1 h, a saturated solution of brine is added and the mixture extracted with ethyl acetate (3×50 mL). The combined extracts are dried ($MgSO_4$) and evaporated to a residue which can be purified by column chromatography (silica) to give the desired product.

By following the above procedure but replacing propanoyl chloride with either acetyl chloride or cyclopropanecarbonyl chloride in Step D the following compounds can be prepared:

1. (R)-N-[[6-(Aminosulfonyl)-4-ethylamino-3,4-dihydro-2H-thieno[3,2-e]-1,2-thiazin-2-yl]propyl]acetamide $S^1,S^1$-dioxide
2. (R)-N-[[6-(Aminosulfonyl)-4-ethylamino-3,4-dihydro-2H-thieno[3,2-e ]-1,2-thiazin-2-yl]propyl]cyclopropylcarboxamide $S^1,S^1$-dioxide
3. (R)-N-[[6-(Aminosulfonyl)-4-ethylamino-3,4-dihydro-2H-thieno[3,2-e]-1,2-thiazin-2-yl]propyl]-3-methoxy propanamide $S^1,S^1$-dioxide

EXAMPLE 11

| Ophthalmic Solution | |
| --- | --- |
| Ingredient | Concentration (wt %) |
| R-(+)-6-(Aminosulfonyl)-4-ethylamino-3,4-dihydro-2H-thieno[3,2-e]-1,2-thiazine-2-butanoic acid 1,1-dioxide ethyl ester hydrochloride (Compound) | 2.0% |
| Hydroxyethylcellulose | 0.5% |
| Monobasic Sodium Phosphate | 0.13% |
| Dibasic Sodium Phosphate | 0.01% |
| Benzalkonium Chloride | 0.01% |
| Disodium Edetate | 0.01% |
| Purified Water | q.s. |
| NaCl (Osmolality = 282 mOsm) | 0.4% |
| HCl/NaOH | pH 5.0 |

The Compound and sodium chloride are mixed together in water and the pH of the solution is adjusted to 5.02 by the addition of 1N NaOH. The hydroxyethylcellulose vehicle is prepared by mixing together monobasic sodium phosphate, dibasic sodium phosphate, and disodium edetate in water. The benzalkonium chloride and hydroxyethylcellulose are added to the mixture and the pH is adjusted to 5.0 by the addition of 1N HCl. A portion of this vehicle is added to the solution containing the Compound and the pH is adjusted to 5.0 by the addition of 1N NaOH.

EXAMPLE 12

| Ophthalmic Gel | |
| --- | --- |
| Ingredient | Concentration (wt %) |
| R-(+)-4-Ethylamino-3,4-dihydro-2-[3-(2-methyl-1-oxo-propoxy)propyl]-2H-thieno[3,2-e]-1,2-thiazine-6-sulfonamide 1,1-dioxide hydrochloride (Compound) | 1.0% |
| Mannitol | 3.6% |
| Benzalkonium Chloride | 0.01% |
| Carbopol | 3.0% |
| HCl/NaOH | pH 5.0 |
| Purified Water | q.s. |

The mannitol, benzalkonium chloride, Compound, and carbopol are added to water and mixed well. The pH is adjusted to pH 5.0 and purified water (q.s. to 5 mL) is added and mixed well to form a gel.

EXAMPLE 13

| Ophthalmic Solution | |
| --- | --- |
| Ingredient | Concentration (wt %) |
| R-(+)-6-(Aminosulfonyl)-4-ethylamino-3,4-dihydro-2H-thieno[3,2-e]-1,2-thiazine-2-butanoic acid 1,1-dioxide ethyl ester hydrochloride (Compound) | 2.27% |
| Hydroxypropylmethylcellulose | 3.3% |
| Sodium Acetate Dehydrate | 0.1% |
| Mannitol (Osmolality - 282 mOsm) | 2.44% |
| Benzalkonium Chloride | 0.01% |
| Disodium Edetate | 0.01% |
| Purified Water | q.s. |
| HCl/NaOH | pH 5.0 |

The sodium acetate, disodium edta, benzylalkonium chloride, and mannitol are dissolved in water for injection. The pH is adjusted to 5.0 with 1N sodium hydroxide and the final volume is adjusted with water for injection. Hydroxypropylmethylcellulose is mixed with the acetate buffer solution to furnish the vehicle. To prepare the final formulation, the Compound is diluted with vehicle and the pH is adjusted to 5.0 with 1N sodium hydroxide.

EXAMPLE 14

OPHTHALMIC SUSPENSION

| Ingredient | Concentration (wt %) |
| --- | --- |
| R-(+)-6-(Aminosulfonyl)-N-ethyl-4-ethylamino-3,4-dihydro-2H-thieno[3,2-e]-1,2-thiazine-2-butanamide 1,1-dioxide (Compound) | 2.0% |
| Hydroxypropylmethylcellulose | 3.0% |
| Sodium acetate (trihydrate) | 0.1% |
| Mannitol | 4.1% |
| Disodium EDTA | 0.01% |
| Benzalkonium Chloride Solution | 0.01% + 5% xs |
| Sodium Hydroxide | q.s. pH = 5.0 |
| Hydrochloric Add | q.s. pH = 5.0 |
| Water for Injection | q.s. 100% |

The above ingredients are mixed together in a manner similar to the procedure described in Example 13 to furnish the ophthalmic suspension.

EXAMPLE 15

OPHTHALMIC SUSPENSION

| Ingredient | Concentration (wt %) |
| --- | --- |
| R-(+)-6-(Aminosulfonyl)-N-ethyl-4-ethylamino-3,4-dihydro-2H-thieno[3,2-e]-1,2-thiazine-2-butanamide 1,1-dioxide (Compound) | 2.0% |
| Carbomer 934P | 0.5% |
| Sodium Chloride | 0.4% |
| Mannitol | 2.4% |
| Disodium EDTA | 0.01% |
| Polysorbate 80 | 0.05% |
| Benzalkonium Chloride Solution | 0.01% + 5% xs |
| Sodium Hydroxide | q.s. pH = 7.2 |
| Hydrochloric Acid | q.s. pH = 7.2 |
| Water for Injection | q.s. 100% |

The above ingredients are mixed together using a method similar to the procedure described in Example 13 to furnish the ophthalmic suspension.

We claim:

1. A compound of the formula

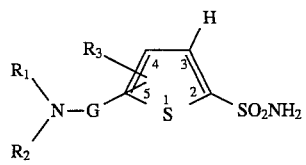

or a pharmaceutically acceptable salt thereof wherein:

$R_1$ and $R_3$ are each saturated carbon atoms joined together to form a ring of 6 members in which said carbon atoms can be unsubstituted or substituted optionally with $R_4$;

$R_2$ is $C_{1-8}$ alkyl substituted with $C(=O)R_7$; or $C_{2-8}$ alkyl substituted with $OC(=O)R_7$, or $NHC(=O)R_7$;

$R_4$ is OH; $C_{1-4}$ alkyl unsubstituted or substituted optionally with OH, $NR_5R_6$, halogen, $C_{1-4}$ alkoxy or $C(=O)R_7$; $C_{1-4}$ alkoxy; $C_{2-4}$ alkoxy substituted optionally with OH, $NR_5R_6$, halogen, $C_{1-4}$ alkoxy or $C(=O)R_7$; $NR_5R_6$; phenyl or $R_{10}$ either of which can be unsubstituted or substituted optionally with OH, $(CH_2)_nNR_5R_6$, halogen, $C_{1-4}$ alkoxy, $C_{1-4}$ haloalkoxy, $C(=O)R_7$, $S(=O)_mR_8$ or $SO_2NR_5R_6$, wherein m is 0–2 and n is 0–2;

$R_5$ and $R_6$ are the same or different and are H; $C_{1-6}$ alkyl; $C_{2-6}$ alkyl substituted optionally with OH, halogen, $C_{1-4}$ alkoxy or $C(=O)R_7$; hydroxy; $C_{1-4}$ alkoxy; $C_{2-4}$ alkoxy substituted optionally with OH, halogen, $C_{1-4}$ alkoxy or $C(=O)R_7$; $C_{3-7}$ alkenyl unsubstituted or substituted optionally with OH, $NR_5R_6$, or $C_{1-4}$ alkoxy; $C_{3-7}$ -alkynyl unsubstituted or substituted optionally with OH, $NR_5R_6$, or $C_{1-4}$ alkoxy; $C_{1-2}$alkyl$C_{3-5}$cycloalkyl; $C(=O)R_7$ or $R_5$ and $R_6$ can be joined to form a ring selected from the group consisting of pyrrolidine, oxazolidine, thiomorpholine, thiomorpholine 1,1 dioxide, morpholine, piperazine, and thiazolidine 1,1-dioxide, which can be unsubstituted or substituted optionally on carbon with OH, (=O), halogen, $C_{1-4}$ alkoxy, $C(=O)R_7$, $C_{1-6}$ alkyl, $C_{1-6}$ alkyl substituted optionally with OH, halogen, $C_{1-4}$ alkoxy, $C(=O)R_7$ or on nitrogen with $C_{1-4}$ alkoxy, $C(=O)R_7$, $S(=O)_mR_8$, $C_{1-6}$ alkyl or $C_{2-6}$ alkyl substituted optionally with OH, halogen, $C_{1-4}$ alkoxy, $C(=O)R_7$ or on sulfur by $(=O)_m$, wherein m is 0–2;

$R_7$ is $C_{1-8}$ alkyl; $C_{1-8}$ alkyl substituted optionally with OH, $NR_5R_6$, halogen, $C_{1-4}$ alkoxy or $C(=O)R_9$; $C_{1-4}$ alkoxy; $C_{2-4}$ alkoxy substituted optionally with OH, $NR_5R_6$, halogen or $C_{1-4}$ alkoxy; $NR_5R_6$; or phenyl or $R_{10}$ either of which can be unsubstituted or substituted optionally with OH, halogen, $C_{1-3}$ alkyl, $C_{1-3}$ haloalkoxy, $(CH_2)_nNR_5R_6$, $S(=O)_mR_8$ or $SO_2NR_5R_6$, wherein n is 0 or 1 and m is 0–2;

$R_8$ is $C_{1-4}$ alkyl; $C_{2-4}$ alkyl substituted optionally with OH, $NR_5R_6$, halogen, $C_{1-4}$ alkoxy or $C(=O)R_7$;

$R_9$ is $C_{1-4}$ alkyl; $C_{1-4}$ alkoxy; amino, $C_{1-3}$ alkylamino, or di-$C_{1-3}$ alkylamino;

$R_{10}$ is a monocyclic ring system selected from the group consisting of furan, thiophene, pyrrole, pyrazole, imidazole, triazole, tetrazole, oxazole, isoxazole, isothiazole, thiazole, thiadiazole, pyridine, pyrimidine, pyridazine, and pyrazine; and G is $SO_2$.

2. The compound of claim 1 selected from the group consisting of R-(+)-6-(Aminosulfonyl)-4-ethylamino-3,4-dihydro-2H-thieno[3,2-e]-1,2-thiazine-2-butanoic acid 1,1-dioxide ethyl ester hydrochloride; R-(+)-6-(Aminosulfonyl)-4-ethylamino-3,4-dihydro-2H-thieno[3,2-e]-1,2-thiazine-2-butanoic acid 1,1-dioxide 1-methylethyl ester hydrochloride; R-(+)-6-(Aminosulfonyl)-4-ethylamino-3,4-dihydro-2H-thieno[3,2-e]-1,2-thiazine-2-propanoic acid 1,1-dioxide 1-methylethyl ester hydrochloride; R-(+)-6-(Aminosulfonyl)-4-ethylamino-3,4-dihydro-2H-thieno[3,2-e]-1,2-thiazine-2-propanoic acid 1,1-dioxide ethyl ester hydrochloride; R-(+)-4-Ethylamino-3,4-dihydro-2-(3-acetyloxypropyl)-2H-thieno[3,2-e]-1,2-thiazine-6-sulfonamide 1,1-dioxide hydrochloride; R-(+)-4-Ethylamino-3,4-dihydro-2-[3-(2-methyl-1-oxo-propoxy)propyl]-2H-thieno[3,2-e]-1,2thiazine-6-sulfonamide 1,1-dioxide hydrochloride; R-(+)-2-(3-acetyloxypropyl)-3,4-dihydro-4-propylamino-2H-thieno[3,2-e]-1,2-thiazine-6-sulfonamide 1,1-dioxide;R-(+)-4-Ethylamino-3,4-dihydro-2-[2-(2-methyl-1-oxo-propoxy)ethyl]-2H-thieno[3,2-e]-1,2-thiazine-6-sulfonamide 1,1-dioxide hydrochloride; R-(+)-4-Ethylamino-3,4-dihydro-2-(2-acetyloxyethyl)-2H-thieno[3,2-e]-1,2-thiazine-6-sulfonamide 1,1-dioxide hydrochloride; R-(+)-2-[6-(Aminosulfonyl)-4-ethylamino-3,4-dihydro-2H-thieno 3,2-e]-1,2-thiazin-2-yl]ethylcyclopropane-carboxylate $S^1,S^1$-dioxide hydrochloride; (R)-4-Ethylamino-3,4-dihydro-2-[4-methoxyphenylcarbonyloxy)propyl]-2H-thieno[3,2e]-1,2-thiazine-6-sulfonamide 1,1-dioxide; (R)-4-Ethylamino-3,4-dihydro- 2-[(3-methoxy-1-oxo-propoxy)ethyl]-2H-thieno[3,2-e]-1,2-thiazine-6-sulfonamide 1,1-dioxide; (R)-4-Ethylamino-3,4-dihydro-2-[(3-hydoxy-1-oxo-propoxy)ethyl]-2H-thieno[3,2-e]-1,2-thiazine-6-sulfonamide 1,1-dioxide; R-(+)-6-(Aminosulfonyl)-N-ethyl-4-ethylamino-3,4-dihydro-2H-thieno[3,2-e]-1,2-thiazine-2-butanamide 1,1-dioxide; R-(+)-6-(Aminosulfonyl)-N-ethyl-4-ethylamino-3,4-dihydro-2H-thieno[3,2-e]-1,2-thiazine-2-propanamide 1,1-dioxide hydrochloride; (R)-6-(Aminosulfonyl)-N-(2-methoxyethyl)-4-ethylamino-3,4-dihydro-2H-thieno[3,2-e]-1,2-thiazine-2-propanamide 1,1-dioxide; (R)-6-(Aminosulfonyl)-N-methyl-4-ethylamino-3,4-dihydro-2H-thieno[3,2-e]-1,2-thiazine-2-propanamide 1,1-dioxide; (R)-6-(Aminosulfonyl)-N-cyclopropyl-4-ethylamino-3,4-dihydro-2H-thieno[3,2-e]-1,2-thiazine-2-propanamide 1,1-dioxide; (R)-N-[[[6-(Aminosulfonyl)-4-ethylamino-3,4-dihydro-2H-thieno[3,2-e]-1,2-thiazin-2-yl]ethyl]carbonyl]-alanine ethyl ester $S^1,S^1$-dioxide; (R)-N-[[6-(Aminosulfonyl)-4-ethylamino-3,4-dihydro-2H-thieno[3,2-e]-1,2-thiazin-2-yl]propyl]propanamide $S^1,S^1$-dioxide; (R)-N-[[6-(Aminosulfonyl)-4-ethylamino-3,4-dihydro-2H-thieno[3,2-e]-1,2-thiazin-2-yl]propyl]acetamide $S^1,S^1$-dioxide; (R)-N-[[6-(Aminosulfonyl)-4-ethylamino-3,4-dihydro-2H-thieno[3,2-e]-1,2-thiazin-2-yl]propyl]cyclopropyl-carboxamide $S^1,S^1$-dioxide; (R)-N-[[6-(Aminosulfonyl)-4-ethylamino-3,4-dihydro-2H-thieno[3,2-e]-1,2-thiazin-2-yl]propyl]-3-methoxy propanamide $S^1,S^1$-dioxide.

3. The compound of claim 2 which is R-(+)-6-(Aminosulfonyl)-4-ethylamino-3,4-dihydro-2H-thieno[3,2-e]-1,2-thiazine-2-butanoic acid 1,1-dioxide ethyl ester hydrochloride.

4. The compound of claim 2 which is R-(+)-6-(Aminosulfonyl)-4-ethylamino-3,4-dihydro-2H-thieno[3,2-e]-1,2-thiazine-2-butanoic acid 1,1-dioxide1-methyester hydrochloride.

5. A topical ophthalmic formulation for controlling intraocular pressure comprising a pharmaceutically effective amount of the compound of claim 1 in an inert carrier.

6. A method for controlling intraocular pressure by administering a pharmaceutically effective amount of the compound of claim 1 to a human eye.

* * * * *

UNITED STATES PATENT AND TRADEMARK OFFICE
Certificate

Patent No. 5,585,377                                                                 Patented: December 17, 1996

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Thomas R. Dean, Weatherford, TX; Jesse A. May, Fort Worth, TX; Hwang-Hsing Chen, Fort Worth, TX; Abdelmoula Namil, Arlington, TX; and Anura Dantanarayana, Fort Worth, TX Signed and Sealed this Third Day of June 2003.

JOHN M. FORD
*Supervisory Patent Examiner*
Art Unit 1611